United States Patent [19]

Kehne et al.

[11] Patent Number: 5,104,443
[45] Date of Patent: Apr. 14, 1992

[54] HETEROCYCLIC 2-ALKOXYPHENOXYSULFONYLUREAS AND THE USE THEREOF AS HERBICIDES OR PLANT GROWTH REGULATORS

[75] Inventors: Heinz Kehne, Hofheim am Taunus; Lothar Willms, Hillscheid; Klaus Bauer, Hanau; Hermann Bieringer, Eppstein/Taunus; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 352,167

[22] Filed: May 15, 1989

[30] Foreign Application Priority Data

May 17, 1988 [DE] Fed. Rep. of Germany ....... 3816704

[51] Int. Cl.$^5$ .................. A01N 43/54; C07D 239/26; C07D 239/69; C07D 239/42
[52] U.S. Cl. ........................ 71/92; 544/321; 544/323; 544/319; 544/335; 544/332
[58] Field of Search ............... 71/92; 544/321, 323, 544/319, 335, 332

[56] References Cited

U.S. PATENT DOCUMENTS 4,191,553 3/1980 Reap .......................... 71/92
4,480,101 10/1984 Meyer ....................... 544/320

FOREIGN PATENT DOCUMENTS 0004163 9/1979 European Pat. Off. .
4163 9/1979 European Pat. Off. .
0141199 5/1985 European Pat. Off. .
3151450 7/1983 Fed. Rep. of Germany .
62-155202 7/1987 Japan .
2133790 8/1984 United Kingdom .

OTHER PUBLICATIONS

AA Gerhard Lohaus, "Darstellung und Umsetzungen von Aryloxysulfonlyisocyanaten", Chem. Ber. 105, pp. 2791 to 2799 (1972).
Chemical Abstracts 108:200229s Kato et al. (1988).
Chemical Abstracts 108: 33622f Kato et al. (1988).

*Primary Examiner*—John M. Ford
*Attorney, Agent, or Firm*—Curtis, Morris & Safford

[57] ABSTRACT

Compounds of the formula I or salts thereof

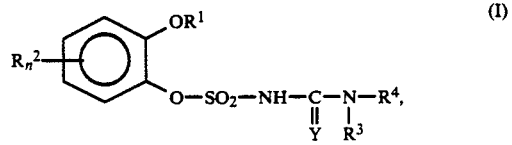

where
$R^1$ is ethyl, propyl or isopropyl,
$R^2$ is halogen, $NO_2$, $CF_3$, CN, alkyl, alkoxy, alkylthio or alkoxycarbonyl,
n is 0, 1, 2 or 3, Y is O or S,
$R^3$ is hydrogen, alkyl, alkenyl, alkynyl or alkoxy;
$R^4$ is a heterocyclic radical of the formulae

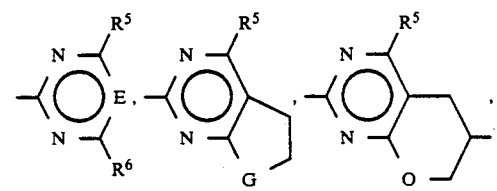

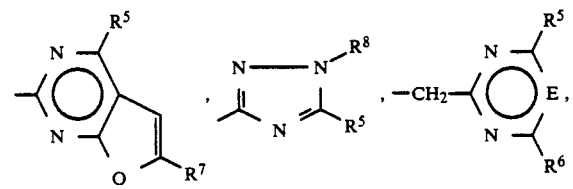

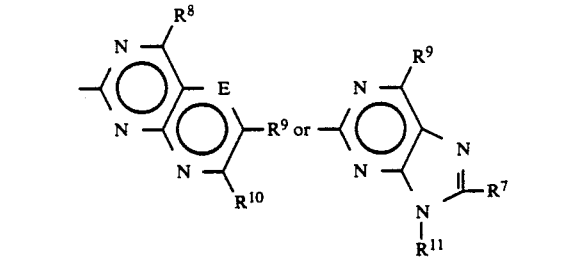

E is CH or N; G is O or $CH_2$,
$R^5$ and $R^6$ are hydrogen, halogen, or are alkyl, alkoxy or alkylthio, which are optionally substituted by halogen, alkoxy or alkylthio, or are $-NR^{12}R^{13}$, $-OCHR^7-CO_2R^{12}$, ($C_3-C_6$cycloalkyl, ($C_3-C_5$)alkenyl, ($C_2-C_4$)-alkynyl, ($C_3-C_5$)alkenyloxy or ($C_3-C_5$(alkynyloxy; $R^7$ is hydrogen or alkyl, $R^8$ is alkyl, $-CHF_2$or $-CH_2CF_3$; $R^9$ and $R^{10}$ are hydrogen, alkyl, alkoxy or halogen; $R^{11}$ is hydrogen, alkyl, $-CHF_2$ or $CH_2CF_3$; $R^{12}$ and $R^{13}$ independently of one another are hydrogen, alkyl, alkenyl or alkynyl, possess outstanding herbicidal and plant growth-regulating properties.

18 Claims, No Drawings

HETEROCYCLIC 2-ALKOXYPHENOXYSULFONYLUREAS AND THE USE THEREOF AS HERBICIDES OR PLANT GROWTH REGULATORS

DESCRIPTION

It is known that heterocyclically substituted phenoxysulfonylureas possess herbicidal and plant growth-regulating properties (EP-A 4,163, DE-A 3,151-450).

Surprisingly, it has now been found that heterocyclically substituted sulfamic acid phenyl esters, the phenyl ester moiety of which is formed by selected pyrocatechol monoalkyl ethers, are particularly suitable as herbicides or plant growth regulators.

The present invention therefore relates to compounds of the formula (I) or the salts thereof

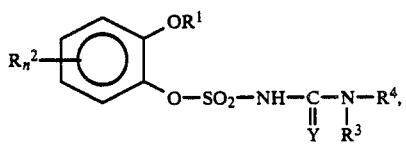

where $R^1$ is ethyl, propyl or isopropyl, $R^2$ is halogen, $NO_2$, $CF_3$, $CN$, $(C_1-C_4)$alkyl, $(C_1-C_4)$alkoxy, $(C_1-C_4)$alkylthio or $(C_1-C_4$-alkoxy)carbonyl, n is 0, 1, 2 or 3, Y is O or S, $R^3$ is hydrogen, $(C_1-C_8)$alkyl, $(C_2-C_8)$alkenyl, $(C_2-C_8)$alkynyl or $(C_1-C_4)$alkoxy;

$R^4$ is a heterocyclic radical of the formulae

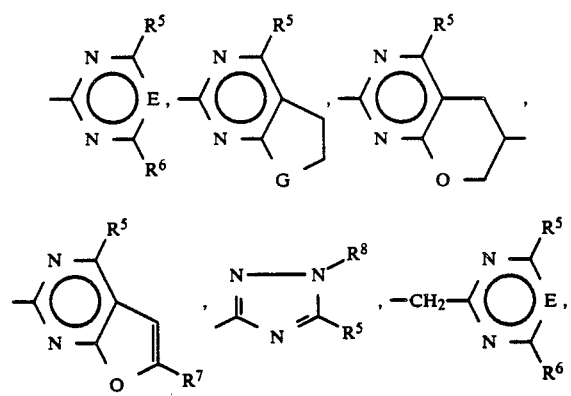

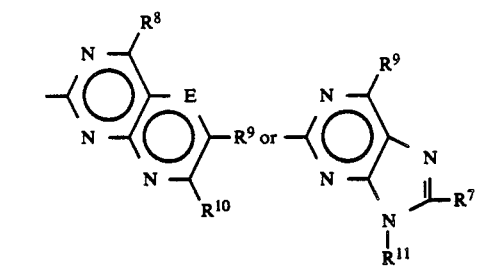

E is CH or N,

G is O or $CH_2$, $R^5$ and $R^6$ independently of one another are hydrogen, halogen, $(C_1-C_6)$alkyl, $(C_1-C_6)$alkoxy or $(C_1-C_6)$alkylthio, it being possible for the abovementioned radicals to be monosubstituted or polysubstituted by halogen or monosubstituted or disubstituted by $(C_1-C_4)$alkoxy or $(C_1-C_4)$alkylthio, furthermore are a radical of the formula $-NR^{12}R^{13}$, $-OCHR^7-CO_2R^{12}$, $(C_3-C_6)$cycloalkyl, $(C_3-C_5)$alkenyl, $(C_2-C_4)$alkynyl, $(C_3-C_5)$alkenyloxy or $(C_3-C_5)$alkynyloxy, $R^7$ is hydrogen or $(C_1-C_4)$alkyl, $R^8$ is $(C_1-C_4)$alkyl, $-CHF_2$ or $-CH_2CF_3$, $R^9$ and $R^{10}$ independently of one another are hydrogen, $(C_1-C_4)$alkyl, $(C_1-C_5)$alkoxy or halogen, $R^{11}$ is hydrogen, $(C_1-C_4)$alkyl, $-CHF_2$ or $CH_2CF_3$ and $R^{12}$ and $R^{13}$ independently of one another are hydrogen, $(C_1-C_4)$alkyl, $(C_2-C_4)$alkenyl or $(C_3-C_4)$alkynyl.

The compounds of the formula (1) can form salts in which the hydrogen of the $-SO_2-NH-$ group is replaced by a cation which is suitable for agriculture. In general, these salts are metal salts, in particular alkali metal salts, alkaline earth metal salts, optionally alkylated ammonium salts or organic amine salts.

In the above definitions, halogen is preferably fluorine, chlorine or bromine.

Preferred compounds of the formula I or salts thereof are those in which n=0 or 1, Y is O, $R^2$ is orientated in the 6-position of the phenyl ring and has the above-mentioned meaning, in the case of halogen in particular F or Cl, $R^3$ is hydrogen, $(C_1-C_4)$alkyl or $(C_3-C_4)$alkenyl, $R^4$ is a heterocyclic radical of the formula

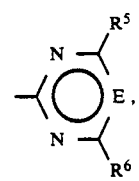

E is CH or N and $R^5$ and $R^6$ are halogen, $(C_1-C_4)$alkyl, $(C_1-C_4)$alkoxy or $(C_1-C_4)$alkylthio, each of which can be substituted as described above.

Particularly preferred compounds of the formula (I) or salts thereof are those where n=0 or 1, $R^2$ is orientated in the 6-position of the phenyl ring and is fluorine, chlorine, $(C_1-C_4)$alkyl, $(C_1-C_4)$alkoxy or $(C_1-C_4)$alkoxycarbonyl, $R^3$ is hydrogen or methyl, $R^4$ is a heterocyclic radical of the formula

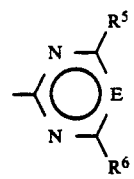

E is CH or N and $R^5$ and $R^6$ independently of one another are chlorine, bromine, $(C_1-C_4)$alkyl, $(C_1-C_4)$alkoxy, $OCHF_2$ or $OCH_2CF_3$ or $CF_3$, in particular $(C_1-C_2)$alkyl or $(C_1-C_2)$alkoxy.

The present invention furthermore relates to processes for the preparation of the compounds of the general formula (I) or salts thereof, which comprise reacting (a) a compound of the formula (II)

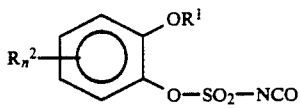

with a compound of the formula (III)

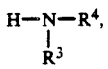

or
(b) a compound of the formula (IV)

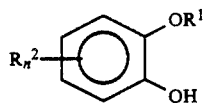

with a chlorosulfonylurea of the formula (V)

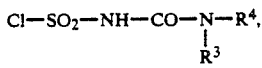

or
(c) a compound of the formula (VI)

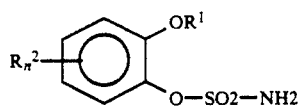

with a carbamate of the formula (VII)

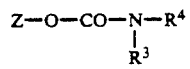

where Z is phenyl or $(C_1-C_6)$alkyl and, if desired, converting the resulting compounds of the formula I into their salts.

The reaction of the compounds of the formulae (II) and (III) is preferably carried out in inert aprotic solvents, such as, for example, acetonitrile, dichloromethane, toluene, tetrahydrofuran or dioxane, at temperatures between 0° C. and the boiling point of the solvent.

The phenoxysulfonyl isocyanates of the formulae (II) can be prepared in a simple manner by processes which are known in principle from the corresponding pyrocatechol monoethers of the formula (IV) and chlorosulfonyl isocyanate (cf. G. Lohaus, Chem. Ber. 105. 2791 (1972)).

The starting substances of the formula (III) are known or can be prepared by processes which are known in principle, for example by cyclizing corresponding guanidine derivatives with appropriately substituted 1,3-diketones, cf., for example, "The Chemistry of Heterocyclic Compounds", Vol. XVI (1962) and Supplement I (1970), or by derivatization of cyanuric chloride, cf., for example, "The Chemistry of Heterocyclic Compounds", L. Rapaport: "s-Triazines and Derivatives" (1959).

The reaction of the compounds (IV) with the chlorosulfonylureas (V) is preferably carried out in inert solvents, such as, for example, dichloromethane, at temperatures between −10° C. and 80° C. in the presence of a base as the HCl-binding agent. Bases which can be employed are alkali metal carbonates, alkali metal bicarbonates, alkaline earth metal carbonates or alkaline earth metal bicarbonates, such as, for example, $K_2CO_3$, $NaHCO_3$ or $Na_2CO_3$, or tertiary amines, such as, for example, pyridine or triethylamine.

The pyrocatechol monoethers (IV) are known from the literature or can be prepared by processes which are known from the literature. The chlorosulfonylureas (V) are accessible from the amines of the formula (III) and chlorosulfonyl isocyanate (EP-A 141,199).

The reaction of the compounds (VI) with the heterocyclic carbamates of the formula (VII) is preferably carried out in the presence of tertiary organic bases, such as, for example, 1,8-diazabicyclo[5.4.0]undec-7-ene (DBU), in inert solvents, such as acetonitrile or dioxane, at temperatures between 20° C. and the boiling point of the solvent (analogously to EP-A 44,807).

The carbamates (VII) which are required for this are known from the literature or are prepared by known processes (EP-A 70,804). The sulfamates (VI) are prepared from the pyrocatechol monoethers on which they are based by known processes (cf., for example, Synthesis 1978, 357; Z. Chem. 15, 270 (1975); Chem. Ber. 105, 2791 (1972)).

The salts of the compounds of the formula I are preferably prepared in inert solvents, such as, for example, water, methanol or acetone, at temperatures from 0°–100° C. Examples of bases which are suitable for the preparation of the salts according to the invention are alkali metal carbonates, such as potassium carbonate, alkali metal hydroxides and alkaline earth metal hydroxides, ammonia or ethanolamine.

The compounds of the formula I according to the invention have an excellent herbicidal activity against a broad range of economically important monocotyledon and dicotyledon noxious plants. The active substances act equally well on perennial weeds which produce shoots from rhizomes, rootstocks or other perennial organs and which cannot be easily controlled. In this context, it does not matter if the substances are applied before sowing, as a pre-emergence treatment or post-emergence treatment. Some representatives of the monocotyledon and dicotyledon weed flora which can be controlled may be mentioned individually as examples, but this is not to be taken to mean a restriction to certain species.

The monocotyledon weed species controlled include, for example, Avena, Lolium, Alopecurus, Phalaris, Echinochloa, Digitaria, Setaria etc. and Cyperus species from the annual group, and the perennial species include Agropyron, Cynodon, Imperata and Sorghum etc., and also perennial Cyperus species. Of the dicotyledon weed species, the range of action covers Galium, Viola, Veronica, Lamium, Stellaria, Amaranthus, Sinapis, Ipomoea, Matricaria, Abutilon, Sida etc. from the annual plants, and Convolvulus, Cirsium, Rumex, Artemisia etc. from the perennial weeds.

Excellent control of weeds occurring under the specific culture conditions in rice, such as, for example, Sagittaria, Alisma, Eleocharis, Scirpus, Cyperus etc., by the active substances according to the invention is also possible.

If the compounds according to the invention are applied to the soil surface before germination, either emergence of the weed seedlings is prevented completely, or the weeds grow until they have reached the cotyledon stage but growth then comes to a standstill and, after a period of three to four weeks, the plants eventually die completely.

When, in the post-emergence method, the active substances are applied to the green parts of the plants, growth also stops dramatically very soon after the treatment, and the weed plants remain in the growth stage of the time of application, or, after a certain period of time, die more or less rapidly so that competition by the weeds, which is detrimental for the crop plants, can thus be prevented at a very early stage and in a sustained manner by using the novel agents according to the invention.

Even though the compounds according to the invention have an excellent herbicidal activity against monocotyledon and dicotyledon weeds, crop plants of economically important crops such as, for example, wheat, barley, rye, rice, maize, sugar beet, cotton and soya beans, are damaged to a negligible extent only, or not at all. Thus, the present compounds are very suitable for selectively controlling undesired plant growth in agricultural plantations of useful plants.

In addition, the compounds according to the invention have plant growth-regulating properties in crop plants. They have a regulating effect on the plant metabolism and can thus employed for facilitating harvesting, such as, for example, by provoking desiccation, abscission and stunted growth. Furthermore, they are suitable for generally regulating and inhibiting undesired vegetative growth, without simultaneously destroying the plants. Inhibition of vegetative growth plays an important role in many monocotyledon and dicotyledon crops because lodging can be reduced hereby, or prevented completely.

The agents according to the invention can be employed in the conventional preparations as wettable powders, emulsifiable concentrates, emulsions, sprayable solutions, dusting agents, seed-dressing agents, dispersions, granules or microgranules.

Wettable powders are preparations which are uniformly dispersible in water and which, in addition to the active substance, also contain wetting agents, for example, polyoxyethylated alkylphenols, polyoxyethylated fatty alcohols, alkylsulfonates or alkylphenylsulfonates, and dispersing agents, for example, sodium ligninsulfonate, sodium 2,2'-dinaphthylmethane-6,6'-disulfonate, sodium dibutylnaphthalenesulfonate and also sodium oleoylmethyltaurinate, as well as, if appropriate, a diluent or inert substance. The formulations are prepared in a customary manner, for example by grinding and mixing of the components.

Emulsifiable concentrates can be prepared, for example, by dissolving the active substance in an inert organic solvent, for example butanol, cyclohexanone, dimethylformamide, xylene and also higher-boiling aromatics or hydrocarbons, with the addition of one or more emulsifiers. In the case of liquid active substances, all or part of the solvent component can be omitted. Emulsifiers which can be used are, for example: calcium salts of alkylarylsulfonic acid, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products alkyl polyglycol ethers, sorbitan fatty acid esters, polyoxyethylene sorbitan fatty acid esters or polyoxyethylene sorbitol esters.

Dusting agents are obtained by grinding the active substance with finely divided solid substances, for example talc or natural clays, such as kaolin, bentonite, pyrophillite, or diatomaceous earth.

Granules can be produced either by spraying the active substance onto adsorptive, granulated inert material or by applying active substance concentrates onto the surface of excipients such as sand, kaolinites or granulated inert material, by means of binders, for example polyvinyl alcohol, sodium polyacrylate or alternatively mineral oils. Suitable active substances can also be granulated in the manner which is conventional for the preparation of fertilizer granules, if desired in a mixture with fertilizers.

The active substance concentration in wettable powders is, for example, about 10 to 90% by weight; the remainder to 100% by weight comprises conventional formulation components. In the case of emulsifiable concentrates, the active substance concentration can be about 5 to 80% by weight. Formulations in the form of dusts usually contain 5 to 20% by weight, sprayable solutions about 2 to 20% by weight. In the case of granules, the active substance content depends partly on whether the active compound is liquid or solid and on which granulation auxiliaries, fillers etc. are used.

In addition, the active substance formulations mentioned contain, if appropriate, the adhesives, wetting agents, dispersing agents, emulsifiers, penetrants, solvents, fillers or carriers which are conventional in each case.

For use, the concentrates, present in commercially available form, are diluted, if appropriate, in a conventional manner, for example using water in the case of wettable powders, emulsifiable concentrates, dispersions and, in some cases, also in the case of microgranules. Preparations in the form of dusts and in the form of granules and also sprayable solutions are usually not further diluted with other inert substances before use.

The application rate required varies with the external conditions, such as temperature, humidity amongst others. It can vary within wide limits between, for example 0.005 and 10.0 kg/ha or more of active substance, preferably, however, it is between 0.01 and 5 kg/ha.

If appropriate, mixtures or mixed formulations with other active substances, such as, for example, insecticides, acaricides, herbicides, fertilizers, growth regulators or fungicides are also possible.

The following examples illustrate the invention in greater detail.

FORMULATION EXAMPLES

A. A dusting agent is obtained by mixing 10 parts by weight of active substance and 90 parts by weight of talc or inert substance, and comminuting the mixture in a hammer mill.

B. A wettable powder which is readily dispersible in water is obtained by mixing 25 parts by weight of active substance, 64 parts by weight of kaolin-containing quartz as inert substance, 10 parts by weight of potassium ligninsulfonte and 1 part by weight of sodium oleoylmethyltaurinate as wetting and dispersing agent, and grinding the mixture in a pinned disk mill.

C. A dispersion concentrate which is readily dispersible in water is obtained by mixing 20 parts by weight of active substance with 6 parts by weight of alkylphenol polyglycol ether (®Triton 207), 3 parts by weight of isotridecanol polyglycol ether (8 EO) and 71 parts by weight of paraffinic mineral oil (boiling range, for example, about 255 to above 377° C.), and grinding the mixture in a ball mill to a fineness of below 5 microns.

D. An emulsifiable concentrate is obtained from 15 parts by weight of active substance, 75 parts by weight of cyclohexanone as solvent and 10 parts by weight of oxyethylated nonylphenol (10 EO) as emulsifier.

CHEMICAL EXAMPLES

EXAMPLE 1

2-Ethoxyphenoxysulfonyl isocyanate 67.9 g (0.48 mol) of chlorosulfonyl isocyanate are added dropwise at 25° C. to a solution of 55.2 g (0.4 mol) of 2-ethoxyphenol in 500 ml of xylene. When the dropwise addition is complete, the temperature is increased slowly to 140° C. and the mixture is refluxed for 2.5 hours. The mixture is cooled, and the solvent as well as excess chlorosulfonyl isocyanate are removed on a rotary evaporator. The yellow oil which remains (97.2 g=100% of theory) is employed without further purification.

EXAMPLE 2

3-(4,6-Dimethoxypyrimidin-2-yl)-1-(2-ethoxyphenoxysulfonyl)urea

A solution of 97.2 g (0.4 mol) of the product of Example 1 in 100 ml of dichloromethane is added dropwise at 25° C. to 62.0 g (0.4 mol) of 2-amino-4,6-dimethoxypyrimidine in 600 ml of dichloromethane. Stirring at room temperature is continued for 16 hours, the mixture is diluted with 600 ml of dichloromethane, and the organic phase is washed twice with 500 ml portions of 2N hydrochloric acid and once with 500 ml of water. After the mixture has been dried using sodium sulfate and after the solvent has been removed on a rotary evaporator, an oily product remains which crystallizes on trituration with diethyl ether. 145.0 g (91% of theory) of 3-(4,6-dimethoxypyrimidin-2-yl)-1-(2-ethoxyphenoxysulfonyl)urea of melting point 145°–147° C. are obtained.

EXAMPLE 3

3-(4,6-dimethoxypyrimidin-2-yl)-1-(2-propoxyphenoxysulfonyl)urea 1.74 g (0.008 mol) of 2-propoxyphenyl sulfamate are added at room temperature to 2.32 g (0.0084 mol) of phenyl N-(4,6-dimethoxypyrimidin-2-yl)carbamate, dissolved in 100 ml of acetonitrile. After 1.33 g (0.0088 mol) of 1,8-diazabicyclo[5.4.0]undec-7-ene (DBU) have been added, the reaction mixture is stirred at room temperature for 18 hours, concentrated, diluted with $H_2O$ and acidified using 2N hydrochloric acid to give a pH of 3–4. After the solids have been filtered off with suction and dried, 2.85 g (86% of theory) of 3-(4,6-dimethoxypyrimidin-2-yl)- 1-(2-propoxyphenoxysulfonyl)urea of melting point 108°–109° C. are obtained.

The compounds of the Tables which follow are prepared as described in Examples 1–3.

TABLE 1

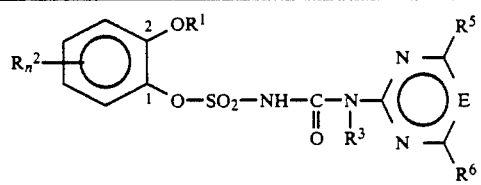

| Ex. No. | $R^1$ | $R^2$ | $R^3$ | $R^5$ | $R^6$ | E | n | m.p. [°C.] |
|---|---|---|---|---|---|---|---|---|
| 4 | $CH_2CH_3$ | | H | $CH_3$ | $CH_3$ | CH | 0 | 162 |
| 5 | $CH_2CH_3$ | | H | $OCH_3$ | $CH_3$ | CH | 0 | 125 |
| 6 | $CH_2CH_3$ | | H | $CH_3$ | $CH_3$ | N | 0 | |
| 7 | $CH_2CH_3$ | | H | $OCH_3$ | $CH_3$ | N | 0 | 128–129 |
| 8 | $CH_2CH_3$ | | H | $OCH_3$ | $OCH_3$ | N | 0 | 169–170 |
| 9 | $CH_2CH_3$ | | H | $OCH_3$ | $SCH_3$ | N | 0 | |
| 10 | $CH_2CH_3$ | | H | $OCH_3$ | Cl | CH | 0 | 134–135 |
| 11 | $CH_2CH_3$ | | H | $OCF_2H$ | $CH_3$ | CH | 0 | |
| 12 | $CH_2CH_3$ | | H | $OCF_2H$ | $OCF_2H$ | CH | 0 | 140 |
| 13 | $CH_2CH_3$ | | H | $OCH_3$ | Br | CH | 0 | |
| 14 | $CH_2CH_3$ | | H | $CH_3$ | Cl | CH | 0 | 163 |
| 15 | $CH_2CH_3$ | | H | $OCH_3$ | H | CH | 0 | |
| 16 | $CH_2CH_3$ | | H | $OCH_3$ | $NHCH_3$ | CH | 0 | |
| 17 | $CH_2CH_3$ | | H | $OCH_3$ | $NHCH_3$ | N | 0 | |
| 18 | $CH_2CH_3$ | | H | $CH_3$ | $NHCH_3$ | CH | 0 | |
| 19 | $CH_2CH_3$ | | H | $OC_2H_5$ | $NHCH_3$ | N | 0 | 168 |
| 20 | $CH_2CH_3$ | | H | $OCH_3$ | $SCH_3$ | CH | 0 | |
| 21 | $CH_2CH_3$ | | H | $OCH_3$ | $OC_2H_5$ | CH | 0 | |
| 22 | $CH_2CH_3$ | | H | $OCH_3$ | $OC_3H_7$ | CH | 0 | |
| 23 | $CH_2CH_3$ | | H | $OCH_3$ | $OC_2H_5$ | N | 0 | |
| 24 | $CH_2CH_3$ | | H | Cl | $OC_2H_5$ | CH | 0 | |
| 25 | $CH_2CH_3$ | | H | $OC_2H_5$ | $OC_2H_5$ | CH | 0 | |
| 26 | $CH_2CH_3$ | | H | $C_2H_5$ | $OCH_3$ | CH | 0 | |
| 27 | $CH_2CH_3$ | | H | $CF_3$ | $OCH_3$ | CH | 0 | |
| 28 | $CH_2CH_3$ | | H | $OCH_2CF_3$ | $CH_3$ | CH | 0 | |
| 29 | $CH_2CH_3$ | | H | $OCH_2CF_3$ | $OCH_3$ | CH | 0 | |
| 30 | $CH_2CH_3$ | | H | $OCH_2CF_3$ | $OCH_2CF_3$ | CH | 0 | |
| 31 | $CH_2CH_3$ | | H | $OCH_2CF_3$ | $NHCH_3$ | CH | 0 | |
| 32 | $CH_2CH_3$ | | H | $OCH_2CF_3$ | $OCH_3$ | N | 0 | 175 |
| 33 | $CH_2CH_3$ | | H | $OCH_2CF_3$ | $NHCH_3$ | N | 0 | |
| 34 | $CH_2CH_3$ | | H | $OCH_3$ | $NHC_2H_5$ | CH | 0 | |
| 35 | $CH_2CH_3$ | | H | $OCH_2CF_3$ | $NHC_2H_5$ | CH | 0 | |
| 36 | $CH_2CH_3$ | | H | $OCH_3$ | $N(CH_3)_2$ | CH | 0 | |
| 37 | $CH_2CH_3$ | | H | $OCH_3$ | $CH(OCH_3)_2$ | CH | 0 | |
| 38 | $CH_2CH_2CH_3$ | | H | $CH_3$ | $CH_3$ | CH | 0 | 113–115 |

TABLE 1-continued

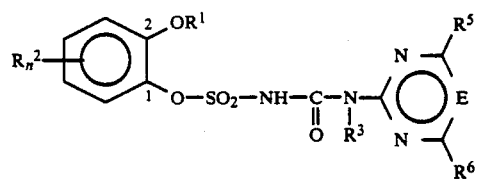

| Ex. No. | $R^1$ | $R^2$ | $R^3$ | $R^5$ | $R^6$ | E | n | m.p. [°C.] |
|---|---|---|---|---|---|---|---|---|
| 39 | $CH_2CH_2CH_3$ | | H | $OCH_3$ | $CH_3$ | CH | 0 | 101–102 |
| 40 | $CH_2CH_2CH_3$ | | H | $CH_3$ | $CH_3$ | N | 0 | |
| 41 | $CH_2CH_2CH_3$ | | H | $OCH_3$ | $CH_3$ | N | 0 | 93–123 |
| 42 | $CH_2CH_2CH_3$ | | H | $OCH_3$ | $OCH_3$ | N | 0 | |
| 43 | $CH_2CH_2CH_3$ | | H | $OCH_3$ | Cl | CH | 0 | 121–123 |
| 44 | $CH_2CH_2CH_3$ | | H | $OCF_2H$ | $CH_3$ | CH | 0 | 126 |
| 45 | $CH_2CH_2CH_3$ | | H | $OCF_2H$ | $OCF_2H$ | CH | 0 | |
| 46 | $CH_2CH_2CH_3$ | | H | $OCH_3$ | Br | CH | 0 | |
| 47 | $CH_2CH_2CH_3$ | | H | $CH_3$ | Cl | CH | 0 | |
| 48 | $CH_2CH_2CH_3$ | | H | $OCH_3$ | H | CH | 0 | |
| 49 | $CH_2CH_2CH_3$ | | H | $OCH_3$ | $NHCH_3$ | CH | 0 | |
| 50 | $CH_2CH_2CH_3$ | | H | $OCH_3$ | $NHCH_3$ | N | 0 | |
| 51 | $CH_2CH_2CH_3$ | | H | CH3 | $NHCH_3$ | CH | 0 | |
| 52 | $CH_2CH_2CH_3$ | | H | $CH_3$ | $NHCH_3$ | N | 0 | |
| 53 | $CH_2CH_2CH_3$ | | H | $OCH_3$ | $SCH_3$ | CH | 0 | |
| 54 | $CH_2CH_2CH_3$ | | H | $OCH_3$ | $OC_2H_5$ | CH | 0 | 127–130 |
| 55 | $CH_2CH_2CH_3$ | | H | $OCH_3$ | $OC_3H_7$ | N | 0 | |
| 56 | $CH_2CH_2CH_3$ | | H | $OCH_3$ | $OC_2H_5$ | N | 0 | |
| 57 | $CH_2CH_2CH_3$ | | H | Cl | $OC_2H_5$ | CH | 0 | |
| 58 | $CH_2CH_2CH_3$ | | H | $OC_2H_5$ | $OC_2H_5$ | CH | 0 | |
| 59 | $CH_2CH_2CH_3$ | | H | $C_2H_5$ | $OCH_3$ | CH | 0 | |
| 60 | $CH_2CH_2CH_3$ | | H | $CF_3$ | $OCH_3$ | CH | 0 | |
| 61 | $CH_2CH_2CH_3$ | | H | $OCH_2CF_3$ | $CH_3$ | CH | 0 | |
| 62 | $CH_2CH_2CH_3$ | | H | $OCH_2CF_3$ | $OCH_3$ | CH | 0 | |
| 63 | $CH_2CH_2CH_3$ | | H | $OCH_2CF_3$ | $OCH_2CF_3$ | CH | 0 | |
| 64 | $CH_2CH_2CH_3$ | | H | $OCH_2CF_3$ | $NHCH_3$ | CH | 0 | |
| 65 | $CH_2CH_2CH_3$ | | H | $OCH_2CF_3$ | $OCH_3$ | N | 0 | |
| 66 | $CH_2CH_2CH_3$ | | H | $OCH_2CF_3$ | $NHCH_3$ | N | 0 | |
| 67 | $CH_2CH_2CH_3$ | | H | $OCH_3$ | $OCH_3$ | CH | 0 | |
| 68 | $CH_2CH_2CH_3$ | | H | $OCH_2CF_3$ | $NHC_2H_5$ | CH | 0 | |
| 69 | $CH_2CH_2CH_3$ | | H | $OCH_3$ | $N(CH_3)_2$ | CH | 0 | |
| 70 | $CH_2CH_2CH_3$ | | H | $OCH_3$ | $CH(OCH_3)_2$ | CH | 0 | |
| 71 | $CH(CH_3)_2$ | | H | $CH_3$ | $CH_3$ | CH | 0 | 90–92 |
| 72 | $CH(CH_3)_2$ | | H | $OCH_3$ | $CH_3$ | CH | 0 | 135–137 |
| 73 | $CH(CH_3)_2$ | | H | $CH_3$ | $CH_3$ | N | 0 | |
| 74 | $CH(CH_3)_2$ | | H | $OCH_3$ | $CH_3$ | N | 0 | 108–110 |
| 75 | $CH(CH_3)_2$ | | H | $OCH_2$ | $OCH_3$ | CH | 0 | 141–143 |
| 76 | $CH(CH_3)_2$ | | H | $OCH_3$ | Cl | CH | 0 | 121–123 |
| 77 | $CH(CH_3)_2$ | | H | $OCF_2H$ | $CH_3$ | CH | 0 | |
| 78 | $CH(CH_3)_2$ | | H | $OCF_2H$ | $OCF_2H$ | CH | 0 | 135–136 |
| 79 | $CH(CH_3)_2$ | | H | $OCH_3$ | Br | CH | 0 | |
| 80 | $CH(CH_3)_2$ | | H | $CH_3$ | Cl | CH | 0 | |
| 81 | $CH(CH_3)_2$ | | H | $OCH_3$ | H | CH | 0 | |
| 82 | $CH(CH_3)_2$ | | H | $OCH_3$ | $NHCH_3$ | CH | 0 | |
| 83 | $CH(CH_3)_2$ | | H | $OCH_3$ | $NHCH_3$ | N | 0 | |
| 84 | $CH(CH_3)_2$ | | H | $CH_3$ | $NHCH_3$ | CH | 0 | |
| 85 | $CH(CH_3)_2$ | | H | $CH_3$ | $NHCH_3$ | N | 0 | |
| 86 | $CH(CH_3)_2$ | | H | $OCH_3$ | $SCH_3$ | CH | 0 | |
| 87 | $CH(CH_3)_2$ | | H | $OCH_3$ | $OC_2H_5$ | CH | 0 | |
| 88 | $CH(CH_3)_2$ | | H | $OCH_3$ | $OC_3H_7$ | CH | 0 | |
| 89 | $CH(CH_3)_2$ | | H | $OCH_3$ | $OC_2H_5$ | N | 0 | |
| 90 | $CH(CH_3)_2$ | | H | Cl | $OC_2H_5$ | CH | 0 | |
| 91 | $CH(CH_3)_2$ | | H | $OC_2H_5$ | $OC_2H_5$ | CH | 0 | |
| 92 | $CH(CH_3)_2$ | | H | $C_2H_5$ | $OCH_3$ | CH | 0 | |
| 93 | $CH(CH_3)_2$ | | H | $CF_3$ | $OCH_3$ | CH | 0 | |
| 94 | $CH(CH_3)_2$ | | H | $OCH_2CF_3$ | $CH_3$ | CH | 0 | |
| 95 | $CH(CH_3)_2$ | | H | $OCH_2CF_3$ | $OCH_3$ | CH | 0 | |
| 96 | $CH(CH_3)_2$ | | H | $OCH_2CF_3$ | $OCH_2CF_3$ | CH | 0 | |
| 97 | $CH(CH_3)_2$ | | H | $OCH_3$ | $OCH_3$ | N | 0 | |
| 98 | $CH(CH_3)_2$ | | H | $OCH_2CF_3$ | $OCH_3$ | N | 0 | |
| 99 | $CH(CH_3)_2$ | | H | $OCH_2CF_3$ | $NHCH_3$ | N | 0 | |
| 100 | $CH(CH_3)_2$ | | H | $OCH_3$ | $NHC_2H_5$ | CH | 0 | |
| 101 | $CH(CH_3)_2$ | | H | $OCH_2CF_3$ | $NHC_2H_5$ | CH | 0 | |
| 102 | $CH(CH_3)_2$ | | H | $OCH_3$ | $N(CH_3)_2$ | CH | 0 | |
| 103 | $CH(CH_3)_2$ | | H | $OCH_3$ | $CH(OCH_3)_2$ | CH | 0 | |
| 104 | $CH_2CH_3$ | 6-Cl | H | $OCH_3$ | $OCH_3$ | CH | 1 | 162–163 |
| 105 | $CH_2CH_3$ | 6-Cl | H | $OCH_3$ | $CH_3$ | CH | 1 | 151–152 |
| 106 | $CH_2CH_3$ | 6-Cl | H | $OCH_3$ | $CH_3$ | N | 1 | 128–129 |
| 107 | $CH_2CH_3$ | 6-Cl | H | $OCH_3$ | Cl | CH | 1 | |
| 108 | $CH_2CH_3$ | 6-F | H | $OCH_3$ | $OCH_3$ | CH | 1 | |
| 109 | $CH_2CH_3$ | 6-F | H | $OCH_3$ | $CH_3$ | CH | 1 | |

TABLE 1-continued

| Ex. No. | R¹ | R² | R³ | R⁵ | R⁶ | E | n | m.p. [°C.] |
|---|---|---|---|---|---|---|---|---|
| 110 | $CH_2CH_3$ | 6-F | H | $OCH_3$ | $CH_3$ | N | 1 | |
| 112 | $CH_2CH_3$ | 6-F | H | $OCH_3$ | Cl | CH | 1 | |
| 113 | $CH_2CH_3$ | 6-Br | H | $OCH_3$ | $OCH_3$ | CH | 1 | |
| 114 | $CH_2CH_3$ | 5-F | H | $OCH_3$ | $OCH_3$ | CH | 1 | |
| 115 | $CH_2CH_3$ | 5-Br | H | $OCH_3$ | $CH_3$ | N | 1 | |
| 116 | $CH_2CH_3$ | 5-Cl | H | $OCH_3$ | Cl | CH | 1 | |
| 117 | $CH_2CH_3$ | 5-Cl | H | $OCH_3$ | $OCH_3$ | CH | 1 | |
| 118 | $CH_2CH_3$ | 4-Cl | H | $OCH_3$ | $CH_3$ | CH | 1 | |
| 119 | $CH_2CH_3$ | 4-F | H | $OCH_3$ | $CH_3$ | N | 1 | |
| 120 | $CH_2CH_3$ | 4-Br | H | $OCH_3$ | Cl | CH | 1 | |
| 121 | $CH_2CH_3$ | 3-Cl | H | $OCH_3$ | $OCH_3$ | CH | 1 | 148–149 |
| 122 | $CH_2CH_3$ | 3-F | H | $OCH_3$ | $CH_3$ | CH | 1 | |
| 123 | $CH_2CH_3$ | 6-$OCH_3$ | H | $OCH_3$ | $CH_3$ | N | 1 | |
| 124 | $CH_2CH_3$ | 6-$OCH_3$ | H | $OCH_3$ | Cl | CH | 1 | |
| 125 | $CH_2CH_3$ | 6-$OCH_3$ | H | $OCH_3$ | $OCH_3$ | CH | 1 | |
| 126 | $CH_2CH_3$ | 6-$OCH_3$ | H | $OCH_3$ | $CH_3$ | CH | 1 | |
| 127 | $CH_2CH_3$ | 5-$OCH_3$ | H | $OCH_3$ | $CH_3$ | N | 1 | |
| 128 | $CH_2CH_3$ | 5-$OCH_3$ | H | $OCH_3$ | Cl | CH | 1 | |
| 129 | $CH_2CH_3$ | 4-$OCH_3$ | H | $OCH_3$ | $OCH_3$ | CH | 1 | |
| 130 | $CH_2CH_3$ | 4-$OCH_3$ | H | $OCH_3$ | $CH_3$ | CH | 1 | |
| 131 | $CH_2CH_3$ | 3-$OCH_3$ | H | $OCH_3$ | $CH_3$ | N | 1 | |
| 132 | $CH_2CH_3$ | 3-$OCH_3$ | H | $OCH_3$ | Cl | CH | 1 | |
| 133 | $CH_2CH_3$ | 6-$OC_2H_5$ | H | $OCH_3$ | $OCH_3$ | CH | 1 | 194–195 |
| 134 | $CH_2CH_3$ | 6-$OC_3H_7$ | H | $OCH_3$ | $CH_3$ | CH | 1 | |
| 135 | $CH_2CH_3$ | 6-$OC_4H_9$ | H | $OCH_3$ | $CH_3$ | N | 1 | |
| 136 | $CH_2CH_3$ | 6-$SCH_3$ | H | $OCH_3$ | Cl | CH | 1 | |
| 137 | $CH_2CH_3$ | 6-$COOCH_3$ | H | $OCH_3$ | $OCH_3$ | CH | 1 | 163 |
| 138 | $CH_2CH_3$ | 6-$COOCH_3$ | H | $OCH_3$ | $CH_3$ | CH | 1 | 148 |
| 139 | $CH_2CH_3$ | 6-$COOCH_3$ | H | $OCH_3$ | $CH_3$ | N | 1 | |
| 140 | $CH_2CH_3$ | 6-$COOCH_3$ | H | $OCH_3$ | Cl | CH | 1 | 154–156 |
| 141 | $CH_2CH_3$ | 6-$COOC_2H_5$ | H | $OCH_3$ | $OCH_3$ | CH | 1 | 124–125 |
| 142 | $CH_2CH_3$ | 6-$COOC_2H_5$ | H | $OCH_3$ | $CH_3$ | CH | 1 | 128–129 |
| 143 | $CH_2CH_3$ | 5-$COOCH_3$ | H | $OCH_3$ | $CH_3$ | N | 1 | |
| 144 | $CH_2CH_3$ | 5-$COOCH_3$ | H | $OCH_3$ | Cl | CH | 1 | |
| 145 | $CH_2CH_3$ | 4-$COOCH_3$ | H | $OCH_3$ | $OCH_3$ | CH | 1 | |
| 146 | $CH_2CH_3$ | 4-$COOCH_3$ | H | $OCH_3$ | $CH_3$ | CH | 1 | |
| 147 | $CH_2CH_3$ | 3-$COOCH_3$ | H | $OCH_3$ | $CH_3$ | N | 1 | |
| 148 | $CH_2CH_3$ | 3-$COOCH_3$ | H | $OCH_3$ | Cl | CH | 1 | |
| 149 | $CH_2CH_3$ | 6-$COOC_3H_7$ | H | $OCH_3$ | $OCH_3$ | CH | 1 | |
| 150 | $CH_2CH_3$ | 6-$COOC_4H_9$ | H | $OCH_3$ | $CH_3$ | CH | 1 | |
| 151 | $CH_2CH_3$ | 6-$CH_3$ | H | $OCH_3$ | $CH_3$ | N | 1 | 139–140 |
| 152 | $CH_2CH_3$ | 6-$CH_3$ | H | $OCH_3$ | Cl | CH | 1 | |
| 153 | $CH_2CH_3$ | 6-$CH_3$ | H | $OCH_3$ | $OCH_3$ | CH | 1 | 177–178 |
| 154 | $CH_2CH_3$ | 6-$CH_3$ | H | $OCH_3$ | $CH_3$ | CH | 1 | 155–156 (decomp.) |
| 155 | $CH_2CH_3$ | 5-$CH_3$ | H | $OCH_3$ | $CH_3$ | N | 1 | |
| 156 | $CH_2CH_3$ | 5-$CH_3$ | H | $OCH_3$ | Cl | CH | 1 | 82 (decomp.) |
| 157 | $CH_2CH_3$ | 4-$CH_3$ | H | $OCH_3$ | $OCH_3$ | CH | 1 | |
| 158 | $CH_2CH_3$ | 3-$CH_3$ | H | $OCH_3$ | $CH_3$ | CH | 1 | 118–120 |
| 159 | $CH_2CH_3$ | 6-$C_2H_5$ | H | $OCH_3$ | $CH_3$ | N | 1 | 139–141 |
| 160 | $CH_2CH_3$ | 6-$C_3H_7$ | H | $OCH_3$ | Cl | CH | 1 | 122–124 |
| 161 | $CH_2CH_3$ | 6-$C_4H_9$ | H | $OCH_3$ | $OCH_3$ | CH | 1 | |
| 162 | $CH_2CH_3$ | 6-$NO_2$ | H | $OCH_3$ | $CH_3$ | CH | 1 | |
| 163 | $CH_2CH_3$ | 6-$CF_3$ | H | $OCH_3$ | $CH_3$ | N | 1 | 155–156 |
| 164 | $CH_2CH_3$ | 6-CN | H | $OCH_3$ | Cl | CH | 1 | |
| 165 | $CH_2CH_3$ | 6-$SCH_3$ | H | $OCH_3$ | $OCH_3$ | CH | 1 | |
| 166 | $CH_2CH_3$ | 6-$SC_2H_5$ | H | $OCH_3$ | $CH_3$ | CH | 1 | |
| 167 | $CH_2CH_3$ | 6-$SC_5H_9$ | H | $OCH_3$ | $CH_3$ | N | 1 | |
| 168 | $CH_2CH_3$ | 6-$SCH_3$ | H | $OCH_3$ | Cl | CH | 1 | |
| 169 | $CH_2CH_2CH_3$ | 6-Cl | H | $OCH_3$ | $OCH_3$ | CH | 1 | |
| 170 | $CH_2CH_2CH_3$ | 6-Cl | H | $OCH_3$ | $CH_3$ | CH | 1 | |
| 171 | $CH_2CH_2CH_3$ | 6-Cl | H | $OCH_3$ | $CH_3$ | N | 1 | |
| 172 | $CH_2CH_2CH_3$ | 6-Cl | H | $OCH_3$ | Cl | CH | 1 | |
| 173 | $CH_2CH_2CH_3$ | 6-F | H | $OCH_3$ | $OCH_3$ | CH | 1 | |
| 174 | $CH_2CH_2CH_3$ | 6-F | H | $OCH_3$ | $OCH_3$ | CH | 1 | |
| 175 | $CH_2CH_2CH_3$ | 6-F | H | $OCH_3$ | $CH_3$ | N | 1 | |
| 176 | $CH_2CH_2CH_3$ | 6-F | H | $OCH_3$ | Cl | CH | 1 | |
| 177 | $CH_2CH_2CH_3$ | 6-Br | H | $OCH_3$ | $OCH_3$ | CH | 1 | |
| 178 | $CH_2CH_2CH_3$ | 5-F | H | $OCH_3$ | $OCH_3$ | CH | 1 | |
| 179 | $CH_2CH_2CH_3$ | 5-Br | H | $OCH_3$ | $CH_3$ | N | 1 | |
| 180 | $CH_2CH_2CH_3$ | 5-Cl | H | $OCH_3$ | Cl | CH | 1 | |
| 181 | $CH_2CH_2CH_3$ | 5-Cl | H | $OCH_3$ | $OCH_3$ | CH | 1 | |

TABLE 1-continued

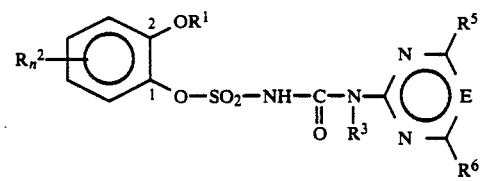

| Ex. No. | R¹ | R² | R³ | R⁵ | R⁶ | E | n | m.p. [°C.] |
|---|---|---|---|---|---|---|---|---|
| 182 | $CH_2CH_2CH_3$ | 4-Cl | H | $OCH_3$ | $CH_3$ | CH | 1 | |
| 183 | $CH_2CH_2CH_3$ | 4-F | H | $OCH_3$ | $CH_3$ | N | 1 | |
| 184 | $CH_2CH_2CH_3$ | 4-Br | H | $OCH_3$ | Cl | CH | 1 | |
| 185 | $CH_2CH_2CH_3$ | 3-Cl | H | $OCH_3$ | $OCH_3$ | CH | 1 | |
| 186 | $CH_2CH_2CH_3$ | 3-F | H | $OCH_3$ | $CH_3$ | CH | 1 | |
| 187 | $CH_2CH_2CH_3$ | 6-$OCH_3$ | H | $OCH_3$ | $CH_3$ | N | 1 | |
| 188 | $CH_2CH_2CH_3$ | 6-$OCH_3$ | H | $OCH_3$ | Cl | CH | 1 | |
| 189 | $CH_2CH_2CH_3$ | 6-$OCH_3$ | H | $OCH_3$ | $OCH_3$ | CH | 1 | |
| 190 | $CH_2CH_2CH_3$ | 6-$OCH_3$ | H | $OCH_3$ | $CH_3$ | CH | 1 | |
| 191 | $CH_2CH_2CH_3$ | 5-$OCH_3$ | H | $OCH_3$ | $CH_3$ | N | 1 | |
| 192 | $CH_2CH_2CH_3$ | 5-$OCH_3$ | H | $OCH_3$ | Cl | CH | 1 | |
| 193 | $CH_2CH_2CH_3$ | 4-$OCH_3$ | H | $OCH_3$ | $OCH_3$ | CH | 1 | |
| 194 | $CH_2CH_2CH_3$ | 4-$OCH_3$ | H | $OCH_3$ | $CH_3$ | CH | 1 | |
| 195 | $CH_2CH_2CH_3$ | 3-$OCH_3$ | H | $OCH_3$ | $CH_3$ | N | 1 | |
| 196 | $CH_2CH_2CH_3$ | 3-$OCH_3$ | H | $OCH_3$ | Cl | CH | 1 | |
| 197 | $CH_2CH_2CH_3$ | 6-$OC_2H_5$ | H | $OCH_3$ | $OCH_3$ | CH | 1 | |
| 198 | $CH_2CH_2CH_3$ | 6-$OC_3H_7$ | H | $OCH_3$ | $CH_3$ | CH | 1 | |
| 199 | $CH_2CH_2CH_3$ | 6-$OC_4H_9$ | H | $OCH_3$ | $CH_3$ | N | 1 | |
| 200 | $CH_2CH_2CH_3$ | 6-$SCH_3$ | H | $OCH_3$ | Cl | CH | 1 | |
| 201 | $CH_2CH_2CH_3$ | 6-$COOCH_3$ | H | $OCH_3$ | $OCH_3$ | CH | 1 | |
| 202 | $CH_2CH_2CH_3$ | 6-$COOCH_3$ | H | $OCH_3$ | $CH_3$ | CH | 1 | |
| 203 | $CH_2CH_2CH_3$ | 6-$COOCH_3$ | H | $OCH_3$ | $CH_3$ | N | 1 | |
| 203a | $CH_2CH_2CH_3$ | 6-$COOCH_3$ | H | $OCH_3$ | Cl | CH | 1 | |
| 204 | $CH_2CH_2CH_3$ | 6-$COOC_2H_5$ | H | $OCH_3$ | $OCH_3$ | CH | 1 | |
| 205 | $CH_2CH_2CH_3$ | 6-$COOC_2H_5$ | H | $OCH_3$ | $CH_3$ | CH | 1 | |
| 206 | $CH_2CH_2CH_3$ | 5-$COOCH_3$ | H | $OCH_3$ | $CH_3$ | N | 1 | |
| 207 | $CH_2CH_2CH_3$ | 5-$COOCH_3$ | H | $OCH_3$ | Cl | CH | 1 | |
| 208 | $CH_2CH_2CH_3$ | 4-$COOCH_3$ | H | $OCH_3$ | $OCH_3$ | CH | 1 | |
| 209 | $CH_2CH_2CH_3$ | 4-$COOCH_3$ | H | $OCH_3$ | $CH_3$ | CH | 1 | |
| 210 | $CH_2CH_2CH_3$ | 3-$COOCH_3$ | H | $OCH_3$ | $CH_3$ | N | 1 | |
| 211 | $CH_2CH_2CH_3$ | 3-$COOCH_3$ | H | $OCH_3$ | Cl | CH | 1 | |
| 212 | $CH_2CH_2CH_3$ | 6-$COOC_3H_7$ | H | $OCH_3$ | $OCH_3$ | CH | 1 | |
| 213 | $CH_2CH_2CH_3$ | 6-$COOC_4H_9$ | H | $OCH_3$ | $CH_3$ | CH | 1 | |
| 214 | $CH_2CH_2CH_3$ | 6-$CH_3$ | H | $OCH_3$ | $CH_3$ | N | 1 | |
| 215 | $CH_2CH_2CH_3$ | 6-$CH_3$ | H | $OCH_3$ | Cl | CH | 1 | |
| 216 | $CH_2CH_2CH_3$ | 6-$CH_3$ | H | $OCH_3$ | $OCH_3$ | CH | 1 | |
| 217 | $CH_2CH_2CH_3$ | 6-$CH_3$ | H | $OCH_3$ | $CH_3$ | CH | 1 | |
| 218 | $CH_2CH_2CH_3$ | 5-$CH_3$ | H | $OCH_3$ | $CH_3$ | N | 1 | |
| 219 | $CH_2CH_2CH_3$ | 5-$CH_3$ | H | $OCH_3$ | Cl | CH | 1 | |
| 220 | $CH_2CH_2CH_3$ | 4-$CH_3$ | H | $OCH_3$ | $OCH_3$ | CH | 1 | |
| 221 | $CH_2CH_2CH_3$ | 3-$CH_3$ | H | $OCH_3$ | $CH_3$ | CH | 1 | |
| 222 | $CH_2CH_2CH_3$ | 6-$C_2H_5$ | H | $OCH_3$ | $CH_3$ | N | 1 | |
| 223 | $CH_2CH_2CH_3$ | 6-$C_3H_7$ | H | $OCH_3$ | Cl | CH | 1 | |
| 224 | $CH_2CH_2CH_3$ | 6-$C_4H_9$ | H | $OCH_3$ | $OCH_3$ | CH | 1 | |
| 225 | $CH_2CH_2CH_3$ | 6-$NO_2$ | H | $OCH_3$ | $CH_3$ | CH | 1 | |
| 226 | $CH_2CH_2CH_3$ | 6-$CF_3$ | H | $OCH_3$ | $CH_3$ | N | 1 | |
| 227 | $CH_2CH_2CH_3$ | 6-CN | H | $OCH_3$ | Cl | CH | 1 | |
| 228 | $CH_2CH_2CH_3$ | 6-$SCH_3$ | H | $OCH_3$ | $OCH_3$ | CH | 1 | |
| 229 | $CH_2CH_2CH_3$ | 6-$SC_2H_5$ | H | $OCH_3$ | $CH_3$ | CH | 1 | |
| 230 | $CH_2CH_2CH_3$ | 6-$SC_5H_9$ | H | $OCH_3$ | $CH_3$ | N | 1 | |
| 231 | $CH_2CH_2CH_3$ | 6-$SCH_3$ | H | $OCH_3$ | Cl | CH | 1 | |
| 232 | $CH(CH_3)_2$ | 6-Cl | H | $OCH_3$ | $OCH_3$ | CH | 1 | |
| 233 | $CH(CH_3)_2$ | 6-Cl | H | $OCH_3$ | $CH_3$ | CH | 1 | |
| 234 | $CH(CH_3)_2$ | 6-Cl | H | $OCH_3$ | $CH_3$ | N | 1 | |
| 235 | $CH(CH_3)_2$ | 6-Cl | H | $OCH_3$ | Cl | CH | 1 | |
| 236 | $CH(CH_3)_2$ | 6-F | H | $OCH_3$ | $OCH_3$ | CH | 1 | |
| 237 | $CH(CH_3)_2$ | 6-F | H | $OCH_3$ | $CH_3$ | CH | 1 | |
| 238 | $CH(CH_3)_2$ | 6-F | H | $OCH_3$ | $CH_3$ | N | 1 | |
| 239 | $CH(CH_3)_2$ | 6-F | H | $OCH_3$ | Cl | CH | 1 | |
| 240 | $CH(CH_3)_2$ | 6-Br | H | $OCH_3$ | $OCH_3$ | CH | 1 | |
| 241 | $CH(CH_3)_2$ | 5-F | H | $OCH_3$ | $CH_3$ | CH | 1 | |
| 242 | $CH(CH_3)_2$ | 5-Br | H | $OCH_3$ | $CH_3$ | N | 1 | |
| 243 | $CH(CH_3)_2$ | 5-Cl | H | $OCH_3$ | Cl | CH | 1 | |
| 244 | $CH(CH_3)_2$ | 5-Cl | H | $OCH_3$ | $OCH_3$ | CH | 1 | |
| 245 | $CH(CH_3)_2$ | 4-Cl | H | $OCH_3$ | $CH_3$ | CH | 1 | |
| 246 | $CH(CH_3)_2$ | 4-F | H | $OCH_3$ | $CH_3$ | N | 1 | |
| 247 | $CH(CH_3)_2$ | 4-Br | H | $OCH_3$ | Cl | CH | 1 | |
| 248 | $CH(CH_3)_2$ | 3-Cl | H | $OCH_3$ | $OCH_3$ | CH | 1 | |
| 249 | $CH(CH_3)_2$ | 3-F | H | $OCH_3$ | $CH_3$ | CH | 1 | |
| 250 | $CH(CH_3)_2$ | 6-$OCH_3$ | H | $OCH_3$ | $CH_3$ | N | 1 | |
| 251 | $CH(CH_3)_2$ | 6-$OCH_3$ | H | $OCH_3$ | Cl | CH | 1 | |

TABLE 1-continued

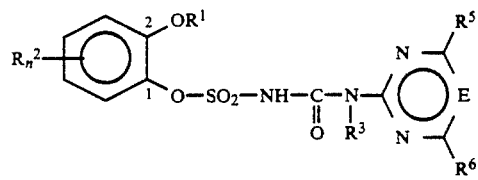

| Ex. No. | $R^1$ | $R^2$ | $R^3$ | $R^5$ | $R^6$ | E | n | m.p. [°C.] |
|---|---|---|---|---|---|---|---|---|
| 252 | $CH(CH_3)_2$ | 6-$OCH_3$ | H | $OCH_3$ | $OCH_3$ | CH | 1 | |
| 253 | $CH(CH_3)_2$ | 6-$OCH_3$ | H | $OCH_3$ | $CH_3$ | CH | 1 | |
| 254 | $CH(CH_3)_2$ | 5-$OCH_3$ | H | $OCH_3$ | $CH_3$ | N | 1 | |
| 255 | $CH(CH_3)_2$ | 5-$OCH_3$ | H | $OCH_3$ | Cl | CH | 1 | |
| 256 | $CH(CH_3)_2$ | 4-$OCH_3$ | H | $OCH_3$ | $OCH_3$ | CH | 1 | |
| 257 | $CH(CH_3)_2$ | 4-$OCH_3$ | H | $OCH_3$ | $CH_3$ | CH | 1 | |
| 258 | $CH(CH_3)_2$ | 3-$OCH_3$ | H | $OCH_3$ | $CH_3$ | N | 1 | |
| 259 | $CH(CH_3)_2$ | 3-$OCH_3$ | H | $OCH_3$ | Cl | CH | 1 | |
| 260 | $CH(CH_3)_2$ | 6-$OC_2H_5$ | H | $OCH_3$ | $OCH_3$ | CH | 1 | |
| 261 | $CH(CH_3)_2$ | 6-$OC_3H_7$ | H | $OCH_3$ | $CH_3$ | CH | 1 | |
| 262 | $CH(CH_3)_2$ | 6-$OC_4H_9$ | H | $OCH_3$ | $CH_3$ | N | 1 | |
| 263 | $CH(CH_3)_2$ | 6-$SCH_3$ | H | $OCH_3$ | Cl | CH | 1 | |
| 264 | $CH(CH_3)_2$ | 6-$COOCH_3$ | H | $OCH_3$ | $OCH_3$ | CH | 1 | |
| 265 | $CH(CH_3)_2$ | 6-$COOCH_3$ | H | $OCH_3$ | $CH_3$ | CH | 1 | |
| 266 | $CH(CH_3)_2$ | 6-$COOCH_3$ | H | $OCH_3$ | $CH_3$ | N | 1 | |
| 267 | $CH(CH_3)_2$ | 6-$COOCH_3$ | H | $OCH_3$ | Cl | CH | 1 | |
| 268 | $CH(CH_3)_2$ | 6-$COOC_2H_5$ | H | $OCH_3$ | $OCH_3$ | CH | 1 | |
| 269 | $CH(CH_3)_2$ | 6-$COOC_2H_5$ | H | $OCH_3$ | $CH_3$ | CH | 1 | |
| 270 | $CH(CH_3)_2$ | 5-$COOCH_3$ | H | $OCH_3$ | $CH_3$ | N | 1 | |
| 271 | $CH(CH_3)_2$ | 5-$COOCH_3$ | H | $OCH_3$ | Cl | CH | 1 | |
| 272 | $CH(CH_3)_2$ | 4-$COOCH_3$ | H | $OCH_3$ | $OCH_3$ | CH | 1 | |
| 273 | $CH(CH_3)_2$ | 4-$COOCH_3$ | H | $OCH_3$ | $CH_3$ | CH | 1 | |
| 274 | $CH(CH_3)_2$ | 3-$COOCH_3$ | H | $OCH_3$ | $CH_3$ | N | 1 | |
| 275 | $CH(CH_3)_2$ | 3-$COOCH_3$ | H | $OCH_3$ | Cl | CH | 1 | |
| 276 | $CH(CH_3)_2$ | 6-$COOC_3H_7$ | H | $OCH_3$ | $OCH_3$ | CH | 1 | |
| 277 | $CH(CH_3)_2$ | 6-$COOC_4H_9$ | H | $OCH_3$ | $CH_3$ | CH | 1 | |
| 278 | $CH(CH_3)_2$ | 6-$CH_3$ | H | $OCH_3$ | $CH_3$ | N | 1 | |
| 279 | $CH(CH_3)_2$ | 6-$CH_3$ | H | $OCH_3$ | Cl | CH | 1 | |
| 280 | $CH(CH_3)_2$ | 6-$CH_3$ | H | $OCH_3$ | $OCH_3$ | CH | 1 | |
| 281 | $CH(CH_3)_2$ | 6-$CH_3$ | H | $OCH_3$ | $CH_3$ | CH | 1 | |
| 282 | $CH(CH_3)_2$ | 5-$CH_3$ | H | $OCH_3$ | $CH_3$ | N | 1 | |
| 283 | $CH(CH_3)_2$ | 5-$CH_3$ | H | $OCH_3$ | Cl | CH | 1 | |
| 284 | $CH(CH_3)_2$ | 4-$CH_3$ | H | $OCH_3$ | $OCH_3$ | CH | 1 | |
| 285 | $CH(CH_3)_2$ | 3-$CH_3$ | H | $OCH_3$ | $CH_3$ | CH | 1 | |
| 286 | $CH(CH_3)_2$ | 6-$C_2H_5$ | H | $OCH_3$ | $CH_3$ | N | 1 | |
| 287 | $CH(CH_3)_2$ | 6-$C_3H_7$ | H | $OCH_3$ | Cl | CH | 1 | |
| 288 | $CH(CH_3)_2$ | 6-$C_4H_9$ | H | $OCH_3$ | $OCH_3$ | CH | 1 | |
| 289 | $CH(CH_3)_2$ | 6-$NO_2$ | H | $OCH_3$ | $CH_3$ | CH | 1 | |
| 290 | $CH(CH_3)_2$ | 6-$CF_3$ | H | $OCH_3$ | $CH_3$ | N | 1 | |
| 291 | $CH(CH_3)_2$ | 6-CN | H | $OCH_3$ | Cl | CH | 1 | |
| 292 | $CH(CH_3)_2$ | 6-$SCH_3$ | H | $OCH_3$ | $OCH_3$ | CH | 1 | |
| 293 | $CH(CH_3)_2$ | 6-$SC_2H_5$ | H | $OCH_3$ | 23 | CH | 1 | |
| 294 | $CH(CH_3)_2$ | 6-$SC_5H_9$ | H | $OCH_3$ | $CH_3$ | N | 1 | |
| 295 | $CH(CH_3)_2$ | 6-$SCH_3$ | H | $OCH_3$ | Cl | CH | 1 | |
| 296 | $CH_2CH_3$ | 4,6-$Cl_2$ | H | $OCH_3$ | Cl | CH | 2 | |
| 297 | $CH_2CH_3$ | 4,6-$Cl_2$ | H | $OCH_3$ | $OCH_3$ | CH | 2 | |
| 298 | $CH_2CH_3$ | 4,6-$Cl_2$ | H | $OCH_3$ | $CH_3$ | N | 2 | |
| 299 | $CH_2CH_3$ | 3,5-$Cl_2$ | H | $OCH_3$ | $OCH_3$ | CH | 2 | |
| 300 | $CH_2CH_2CH_3$ | 4,6-$Cl_2$ | H | $OCH_3$ | Cl | CH | 2 | |
| 301 | $CH_2CH_2CH_3$ | 4,6-$Cl_2$ | H | $OCH_3$ | $OCH_3$ | CH | 2 | |
| 302 | $CH_2CH_2CH_3$ | 4,6-$Cl_2$ | H | $OCH_3$ | $CH_3$ | CH | 2 | |
| 303 | $CH_2CH_2CH_3$ | 3,5-$Cl_2$ | H | $OCH_3$ | $CH_3$ | N | 2 | |
| 304 | $CH(CH_3)_2$ | 4,6-$Cl_2$ | H | $OCH_3$ | $OCH_3$ | CH | 2 | |
| 305 | $CH(CH_3)_2$ | 4,6-$Cl_2$ | H | $OCH_3$ | $OCH_3$ | CH | 2 | |
| 306 | $CH(CH_3)_2$ | 4,6-$Cl_2$ | H | $OCH_3$ | Cl | CH | 2 | |
| 307 | $CH(CH_3)_2$ | 3,5-$Cl_2$ | H | $OCH_3$ | $OCH_3$ | CH | 2 | |
| 308 | $CH_2CH_3$ | 4,6-$F_2$ | H | $OCF_2H$ | $CH_3$ | CH | 2 | |
| 309 | $CH_2CH_3$ | 4,6-$F_2$ | H | $OCH_3$ | $OCH_3$ | CH | 2 | |
| 310 | $CH_2CH_3$ | 4,6-$F_2$ | H | $OCH_3$ | $CH_3$ | N | 2 | |
| 311 | $CH_2CH_3$ | 3,5-$F_2$ | H | $OCH_3$ | $OCH_3$ | CH | 2 | |
| 312 | $CH_2CH_2CH_2$ | 4,6-$F_2$ | H | $OCH_3$ | Cl | CH | 2 | |
| 313 | $CH_2CH_2CH_3$ | 4,6-$F_2$ | H | $OCH_3$ | $OCH_3$ | CH | 2 | |
| 314 | $CH_2CH_2CH_3$ | 4,6-$F_2$ | H | $OCF_2H$ | $OCF_2H$ | CH | 2 | |
| 315 | $CH_2CH_2CH_3$ | 3,5-$F_2$ | H | $OCH_3$ | $OCH_3$ | CH | 2 | |
| 316 | $CH(CH_3)_2$ | 4,6-$F_2$ | H | $OCH_3$ | $CH_3$ | N | 2 | |
| 317 | $CH(CH_3)_2$ | 4,6-$F_2$ | H | $OCH_3$ | $OCH_3$ | CH | 2 | |
| 318 | $CH_2CH_3$ | 4,6-$(CH_3)_2$ | H | $OCH_3$ | Cl | CH | 2 | |
| 319 | $CH_2CH_3$ | 4,6-$(CH_3)_2$ | H | $OCH_3$ | $OCH_3$ | CH | 2 | |
| 320 | $CH_2CH_3$ | 3,5-$(NO_2)_2$ | H | $OCH_2CF_3$ | $OCH_3$ | CH | 2 | |
| 321 | $CH_2CH_3$ | H | $CH_3$ | $OCH_3$ | $OCH_3$ | CH | 0 | 119–120 |
| 322 | $CH_2CH_3$ | H | $CH_3$ | $OCH_3$ | $CH_3$ | N | 0 | 101–102 |

TABLE 1-continued

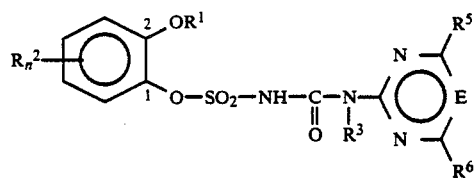

| Ex. No. | R¹ | R² | R³ | R⁵ | R⁶ | E | n | m.p. [°C.] |
|---|---|---|---|---|---|---|---|---|
| 323 | CH₂CH₃ | H | CH₂CH=CH₂ | OCH₃ | OCH₃ | CH | 0 | |
| 324 | CH₂CH₃ | H | CH₂CH=CH₂ | OCH₃ | Cl | CH | 0 | |
| 325 | CH₂CH₂CH₃ | H | CH₃ | OCH₃ | OCH₃ | CH | 0 | |
| 326 | CH₂CH₂CH₃ | H | CH₃ | OCH₃ | CH₃ | CH | 0 | |
| 327 | CH₂CH₂CH₃ | H | CH₂CH=CH₂ | OCH₃ | OCH₃ | CH | 0 | |
| 328 | CH₂CH₂CH₃ | H | CH₂CH=CH₂ | OCH₃ | CH₃ | N | 0 | |
| 329 | CH(CH₃)₂ | H | CH₃ | OCH₃ | OCH₃ | CH | 0 | 127–130 |
| 330 | CH(CH₃)₂ | H | CH₃ | OCH₃ | Cl | CH | 0 | |
| 331 | CH(CH₃)₂ | H | CH₂CH=CH₂ | OCH₃ | OCH₃ | CH | 0 | |
| 332 | CH(CH₃)₂ | H | CH₂CH=CH₂ | OCF₂H | CH₃ | CH | 0 | |
| 333 | CH₂CH₃ | H | C₂H₅ | OCH₃ | OCH₃ | CH | 0 | |
| 334 | CH₂CH₂CH₃ | H | C₂H₅ | OCH₃ | Cl | CH | 0 | |
| 335 | CH(CH₃)₂ | H | C₂H₅ | OCH₃ | OCH₃ | CH | 0 | |
| 336 | CH₂CH₃ | H | C₂H₅ | OCH₂CF₃ | OCH₃ | CH | 0 | |
| 337 | CH₂CH₂CH₃ | H | C₂H₅ | OCH₃ | OCH₃ | CH | 0 | |
| 338 | CH₂CH₃ | 6-CH₃ | CH₃ | OCH₃ | CH₃ | N | 1 | |
| 339 | CH₂CH₂CH₃ | 6-OCH₃ | CH₃ | OCH₃ | OCH₃ | CH | 1 | |
| 340 | CH(CH₃)₂ | 6-Cl | CH₂CH=CH₂ | OCH₃ | Cl | CH | 1 | |
| 341 | CH₂CH₃ | 6-F | CH₂CH=CH₂ | OCH₃ | OCH₃ | CH | 1 | |
| 342 | CH₂CH₂CH₃ | 6-CF₃ | CH₃ | OCH₂CF₃ | OCH₃ | N | 1 | |
| 343 | CH(CH₃)₂ | 6-COOCH₃ | CH₃ | OCH₃ | OCH₃ | CH | 1 | |
| 344 | CH₂CH₃ | 6-C₂H₅ | H | OCH₃ | OCH₃ | CH | 1 | 166–167 |
| 345 | " | " | H | OCH₃ | CH₃ | CH | 1 | 155–156 |
| 346 | " | " | H | OCH₃ | Cl | CH | 1 | |
| 347 | " | " | H | CH₃ | CH₃ | CH | 1 | |
| 348 | " | " | H | OCH₃ | OCH₂CF₃ | N | 1 | |
| 349 | " | " | CH₃ | OCH₃ | OCH₃ | CH | 1 | |
| 350 | " | " | CH₃ | OCH₃ | CH₃ | N | 1 | |
| 351 | " | " | H | OCF₂H | OCF₂H | CH | 1 | |
| 352 | " | " | H | OCH₃ | OCH₃ | N | 1 | |
| 353 | " | 6-C₃H₇ | H | OCH₃ | OCH₃ | CH | 1 | 158 |
| 354 | " | " | H | OCH₃ | CH₃ | CH | 1 | 148 |
| 355 | " | " | H | OCH₃ | CH₃ | N | 1 | 124–126 |
| 356 | " | " | H | OC₂H₅ | NHCH₃ | N | 1 | 167–169 |
| 357 | " | " | H | OCH₃ | OCH₂CF₃ | N | 1 | 115–117 |
| 358 | " | " | H | CH₃ | Cl | CH | 1 | 90 (decomp.) |
| 359 | " | 6-OC₂H₅ | H | OCH₃ | CH₃ | CH | 1 | 157–158 |
| 360 | " | " | H | OCH₃ | Cl | CH | 1 | 158–159 |
| 361 | CH₂CH₃ | 6-OC₂H₅ | H | OCH₃ | CH₃ | N | 1 | 166–167 |
| 362 | " | " | H | CH₃ | CH₃ | CH | 1 | 139–140 |
| 363 | " | " | H | OCH₃ | OCH₂CF₃ | N | 1 | 124 |
| 364 | " | " | CH₃ | OCH₃ | OCH₃ | CH | 1 | 112–115 |
| 365 | " | " | CH₃ | OCH₃ | CH₃ | N | 1 | |
| 366 | " | " | H | OCF₂H | OCF₂H | CH | 1 | |
| 367 | " | " | H | OCH₃ | OCH₃ | N | 1 | 150–151 (decomp.) |
| 368 | " | 6-CF₃ | H | OCH₃ | OCH₃ | CH | 1 | 181 |
| 369 | " | " | H | OCH₃ | CH₃ | CH | 1 | 151–153 |
| 370 | " | " | H | OCH₃ | Cl | CH | 1 | |
| 371 | " | " | H | CH₃ | CH₃ | CH | 1 | |
| 372 | " | " | H | OCH₃ | OCH₂CF₃ | N | 1 | |
| 373 | " | " | CH₃ | OCH₃ | OCH₃ | CH | 1 | |
| 374 | " | " | CH₃ | OCH₃ | CH₃ | N | 1 | |
| 375 | " | " | H | OCF₂H | OCF₂H | CH | 1 | |
| 376 | " | " | H | OCH₃ | OCH₃ | N | 1 | |
| 377 | " | 6-CH₃ | CH₃ | OCH₃ | OCH₃ | CH | 1 | 88 (decomp.) |
| 378 | " | 5-CH₃ | H | OCH₃ | OCH₃ | CH | 1 | 158–161 |
| 379 | " | " | H | OCH₃ | CH₃ | CH | 1 | 113 (decomp.) |
| 380 | " | 5-C₂H₅ | H | OCH₃ | OCH₃ | CH | 1 | |
| 381 | " | " | H | OCH₃ | CH₃ | CH | 1 | |
| 382 | " | 5-Cl | H | OCH₃ | OCH₃ | CH | 1 | |
| 383 | " | " | H | OCH₃ | CH₃ | CH | 1 | |
| 384 | " | 5-OCH₃ | H | OCH₃ | OCH₃ | CH | 1 | |
| 385 | " | " | H | OCH₃ | CH₃ | CH | 1 | |
| 386 | " | 6-CO₂CH₃ | CH₃ | OCH₃ | OCH₃ | CH | 1 | 102–105 (decomp.) |
| 387 | " | " | H | OCH₃ | OCH₃ | N | 1 | 154–155 |
| 388 | CH₂CH₂CH₃ | 6-C₂H₅ | H | OCH₃ | OCH₃ | CH | 1 | |
| 389 | " | " | H | OCH₃ | CH₃ | CH | 1 | |
| 390 | " | " | H | OCH₃ | Cl | CH | 1 | |
| 391 | " | " | H | CH₃ | CH₃ | CH | 1 | |
| 392 | " | " | CH₃ | OCH₃ | OCH₃ | CH | 1 | |
| 393 | " | " | CH₃ | OCH₃ | CH₃ | N | 1 | |

TABLE 1-continued

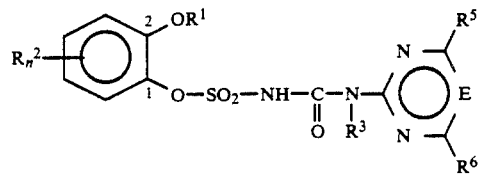

| Ex. No. | R¹ | R² | R³ | R⁵ | R⁶ | E | n | m.p. [°C.] |
|---|---|---|---|---|---|---|---|---|
| 394 | " | " | H | OCF$_2$H | OCF$_2$H | CH | 1 | |
| 395 | " | 6-C$_3$H$_7$ | H | OCH$_3$ | OCH$_3$ | CH | 1 | 143–145 |
| 396 | " | " | H | OCH$_3$ | CH$_3$ | CH | 1 | |
| 397 | " | " | H | OCH$_3$ | CH$_3$ | N | 1 | |
| 398 | " | 6-OC$_2$H$_5$ | H | OCH$_3$ | OCH$_3$ | CH | 1 | 138–139 |
| 399 | " | " | H | OCH$_3$ | Cl | CH | 1 | |
| 400 | " | " | H | OCH$_3$ | CH$_3$ | N | 1 | |
| 401 | " | " | H | CH$_3$ | CH$_3$ | CH | 1 | |
| 402 | " | " | CH$_3$ | OCH$_3$ | OCH$_3$ | CH | 1 | 111–113 |
| 403 | " | " | CH$_3$ | OCH$_3$ | CH$_3$ | N | 1 | |
| 404 | " | " | H | OCF$_2$H | OCF$_2$H | CH | 1 | |
| 405 | " | 6-CF$_3$ | H | OCH$_3$ | OCH$_3$ | CH | 1 | 165–166 |
| 406 | " | " | H | OCH$_3$ | CH$_3$ | CH | 1 | |
| 407 | " | " | H | OCH$_3$ | Cl | CH | 1 | |
| 408 | " | " | H | CH$_3$ | CH$_3$ | CH | 1 | |
| 409 | " | " | CH$_3$ | OCH$_3$ | OCH$_3$ | CH | 1 | |
| 410 | " | " | H | OCF$_2$H | OCF$_2$H | CH | 1 | 121–122 |
| 411 | " | 6-CH$_3$ | CH$_3$ | OCH$_3$ | OCH$_3$ | CH | 1 | |
| 412 | " | 6-CO$_2$CH$_3$ | CH$_3$ | OCH$_3$ | OCH$_3$ | CH | 1 | |
| 413 | CH(CH$_3$)$_2$ | 6-C$_2$H$_5$ | H | OCH$_3$ | OCH$_3$ | CH | 1 | |
| 414 | " | " | H | OCH$_3$ | CH$_3$ | CH | 1 | |
| 415 | " | " | H | OCH$_3$ | Cl | CH | 1 | |
| 416 | " | " | H | CH$_3$ | CH$_3$ | CH | 1 | |
| 417 | " | " | CH$_3$ | OCH$_3$ | OCH$_3$ | CH | 1 | |
| 418 | " | " | CH$_3$ | OCH$_3$ | CH$_3$ | N | 1 | |
| 419 | " | " | H | OCF$_2$H | OCF$_2$H | CH | 1 | |
| 420 | " | 6-C$_3$H$_7$ | H | OCH$_3$ | OCH$_3$ | CH | 1 | 137 |
| 421 | " | " | H | OCH$_3$ | CH$_3$ | CH | 1 | 131–133 |
| 422 | " | " | H | OCH$_3$ | CH$_3$ | N | 1 | |
| 423 | " | 6-OC$_2$H$_5$ | H | OCH$_3$ | OCH$_3$ | CH | 1 | 129–130 |
| 424 | " | " | H | OCH$_3$ | CH$_3$ | CH | 1 | |
| 425 | " | " | H | OCH$_3$ | Cl | CH | 1 | |
| 426 | " | " | H | OCH$_3$ | CH$_3$ | N | 1 | |
| 427 | " | " | H | CH$_3$ | CH$_3$ | CH | 1 | |
| 428 | " | " | CH$_3$ | OCH$_3$ | OCH$_3$ | CH | 1 | |
| 429 | " | " | CH$_3$ | OCH$_3$ | CH$_3$ | N | 1 | |
| 430 | " | " | H | OCF$_2$H | OCF$_2$H | CH | 1 | |
| 431 | " | 6-CF$_3$ | H | OCH$_3$ | OCH$_3$ | CH | 1 | 157–159 |
| 432 | " | " | H | OCH$_3$ | CH$_3$ | CH | 1 | |
| 433 | " | " | H | OCH$_3$ | Cl | CH | 1 | |
| 434 | " | " | H | CH$_3$ | CH$_3$ | CH | 1 | |
| 435 | " | " | CH$_3$ | OCH$_3$ | OCH$_3$ | CH | 1 | |
| 436 | " | " | H | OCF$_2$H | OCF$_2$H | CH | 1 | |
| 437 | " | 6-CH$_3$ | CH$_3$ | OCH$_3$ | OCH$_3$ | CH | 1 | |
| 438 | " | 6-CO$_2$CH$_3$ | CH$_3$ | OCH$_3$ | OCH$_3$ | CH | 1 | |
| 439 | CH$_2$CH$_3$ | 3,4,6-F$_3$ | H | OCH$_3$ | OCH$_3$ | CH | 3 | |
| 440 | " | 6-Cl | C$_2$H$_5$ | OCH$_3$ | OCH$_3$ | CH | 1 | |
| 441 | " | 6-OCH$_3$ | C$_2$H$_5$ | OCH$_3$ | OCH$_3$ | CH | 1 | |
| 442 | " | " | C$_2$H$_5$ | OCH$_3$ | OCH$_3$ | N | 1 | |
| 443 | CH$_2$CH$_2$CH$_2$ | " | C$_2$H$_5$ | OCH$_3$ | OCH$_3$ | N | 1 | |

TABLE 2

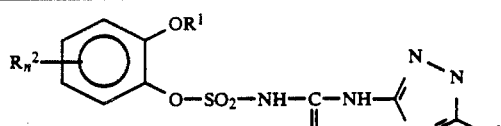

| Ex. No. | R¹ | R² | R⁵ | n | m.p. [°C.] |
|---|---|---|---|---|---|
| 444 | CH$_2$CH$_3$ | H | CH$_3$ | 0 | |
| 445 | CH$_2$CH$_3$ | H | H | 0 | |
| 446 | CH$_2$CH$_3$ | H | OCH$_3$ | 0 | |
| 447 | CH$_2$CH$_2$CH$_3$ | H | CH$_3$ | 0 | |
| 448 | CH$_2$CH$_2$CH$_3$ | H | H | 0 | |
| 449 | CH$_2$CH$_2$CH$_3$ | H | OCH$_3$ | 0 | |
| 450 | CH(CH$_3$)$_2$ | H | CH$_3$ | 0 | |
| 451 | CH(CH$_3$)$_2$ | H | H | 0 | |

TABLE 2-continued

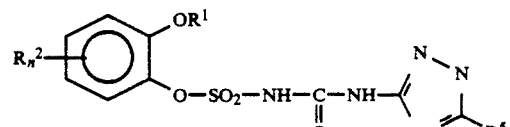

| Ex. No. | R¹ | R² | R⁵ | n | m.p. [°C.] |
|---|---|---|---|---|---|
| 452 | CH(CH$_3$)$_2$ | H | OCH$_3$ | 0 | |
| 453 | CH$_2$CH$_3$ | 6-CH$_3$ | OCH$_3$ | 1 | |
| 454 | CH$_2$CH$_2$CH$_3$ | 6-OCH$_3$ | OCH$_3$ | 1 | |
| 455 | CH(CH$_3$)$_2$ | 6-Cl | OCH$_3$ | 1 | |
| 456 | CH$_2$CH$_3$ | 6-CF$_3$ | OCH$_3$ | 1 | |
| 457 | CH$_2$CH$_2$CH$_3$ | 6-F | OCH$_3$ | 1 | |

TABLE 2-continued

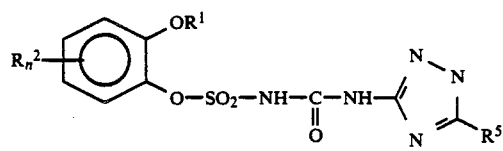

| Ex. No. | R¹ | R² | R⁵ | n | m.p. [°C.] |
|---|---|---|---|---|---|
| 458 | CH(CH₃)₂ | 6-OCF₂H | OCH₃ | 1 | |

TABLE 3

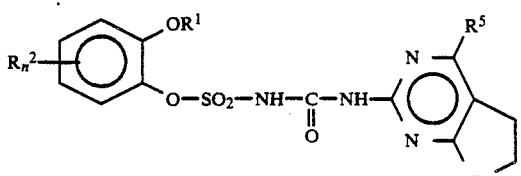

| Ex. No. | R¹ | R² | R⁵ | G | n | m.p. [°C.] |
|---|---|---|---|---|---|---|
| 459 | CH₂CH₃ | H | CH₃ | CH₂ | 0 | |
| 460 | CH₂CH₃ | H | H | CH₂ | 0 | |
| 461 | CH₂CH₃ | H | OCH₃ | CH₂ | 0 | |
| 462 | CH₂CH₂CH₃ | H | CH₃ | CH₂ | 0 | |
| 463 | CH₂CH₂CH₃ | H | H | CH₂ | 0 | |
| 464 | CH₂CH₂CH₃ | H | OCH₃ | CH₂ | 0 | |
| 465 | CH(CH₃)₂ | H | CH₃ | CH₂ | 0 | |
| 466 | CH(CH₃)₂ | H | H | CH₂ | 0 | |
| 467 | CH(CH₃)₂ | H | OCH₃ | CH₂ | 0 | |
| 468 | CH₂CH₃ | H | CH₃ | O | 0 | |
| 469 | CH₂CH₃ | H | H | O | 0 | |
| 470 | CH₂CH₃ | H | OCH₃ | O | 0 | |
| 471 | CH₂CH₂CH₃ | H | CH₃ | O | 0 | |
| 472 | CH₂CH₂CH₃ | H | H | O | 0 | |
| 473 | CH₂CH₂CH₃ | H | OCH₃ | O | 0 | |
| 474 | CH(CH₃)₂ | H | CH₃ | O | 0 | |
| 475 | CH(CH₃)₂ | H | H | O | 0 | |
| 476 | CH(CH₃)₂ | H | OCH₃ | O | 0 | |
| 477 | CH₂CH₃ | 6-CH₃ | CH₃ | CH₂ | 1 | |
| 478 | CH₂CH₂CH₃ | 6-OCH₃ | CH₃ | O | 1 | |
| 479 | CH(CH₃)₂ | 6-Cl | CH₃ | CH₂ | 1 | |
| 480 | CH₂CH₃ | 6-CF₃ | CH₃ | O | 1 | |
| 481 | CH₂CH₂CH₃ | 6-F | CH₃ | CH₂ | 1 | |
| 482 | CH(CH₃)₂ | 6-OCF₂H | CH₃ | O | 1 | |

TABLE 4

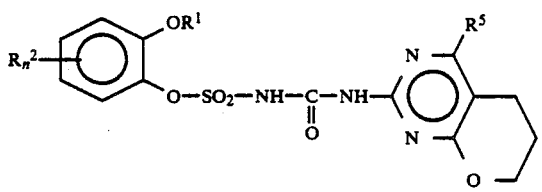

| Ex. No. | R¹ | R² | R⁵ | n | m.p. |
|---|---|---|---|---|---|
| 483 | CH₂CH₃ | H | CH₃ | 0 | |
| 484 | CH₂CH₃ | H | H | 0 | |
| 485 | CH₂CH₃ | H | OCH₃ | 0 | |
| 486 | CH₂CH₂CH₃ | H | CH₃ | 0 | |
| 487 | CH₂CH₂CH₃ | H | H | 0 | |
| 488 | CH₂CH₂CH₃ | H | OCH₃ | 0 | |
| 489 | CH(CH₃)₂ | H | CH₃ | 0 | |
| 490 | CH(CH₃)₂ | H | H | 0 | |
| 491 | CH(CH₃)₂ | H | OCH₃ | 0 | |
| 492 | CH₂CH₃ | 6-CH₃ | OCH₃ | 1 | |
| 493 | CH₂CH₂CH₃ | 6-OCH₃ | OCH₃ | 1 | |
| 494 | CH(CH₃)₂ | 6-Cl | OCH₃ | 1 | |
| 495 | CH₂CH₃ | 6-CF₃ | OCH₃ | 1 | |
| 496 | CH₂CH₂CH₃ | 6-F | OCH₃ | 1 | |
| 497 | CH(CH₃)₂ | 6-OCF₂H | OCH₃ | 1 | |

TABLE 5

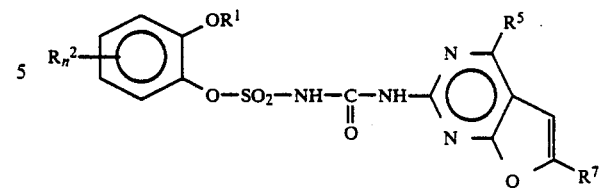

| Ex. No. | R¹ | R² | R⁵ | R⁷ | n | m.p. |
|---|---|---|---|---|---|---|
| 498 | CH₂CH₃ | H | CH₃ | CH₃ | 0 | |
| 499 | CH₂CH₃ | H | H | CH₃ | 0 | |
| 500 | CH₂CH₃ | H | OCH₃ | CH₃ | 0 | |
| 501 | CH₂CH₃ | H | CH₃ | H | 0 | |
| 502 | CH₂CH₂CH₃ | H | CH₃ | CH₃ | 0 | |
| 503 | CH₂CH₂CH₃ | H | H | CH₃ | 0 | |
| 504 | CH₂CH₂CH₃ | H | OCH₃ | CH₃ | 0 | |
| 505 | CH₂CH₂CH₃ | H | CH₃ | H | 0 | |
| 506 | CH(CH₃)₂ | H | CH₃ | CH₃ | 0 | |
| 507 | CH(CH₃)₂ | H | H | CH₃ | 0 | |
| 508 | CH(CH₃)₂ | H | OCH₃ | CH₃ | 0 | |
| 509 | CH(CH₃)₂ | H | CH₃ | H | 0 | |
| 510 | CH₂CH₃ | 6-CH₃ | CH₃ | H | 1 | |
| 511 | CH₂CH₂CH₃ | 6-OCH₃ | CH₃ | CH₃ | 1 | |
| 512 | CH(CH₃)₂ | 6-Cl | CH₃ | H | 1 | |
| 513 | CH₂CH₃ | 6-CF₃ | CH₃ | CH₃ | 1 | |
| 514 | CH₂CH₂CH₃ | 6-F | CH₃ | H | 1 | |
| 515 | CH(CH₃)₂ | 6-OCF₂H | CH₃ | CH₃ | 1 | |

TABLE 6

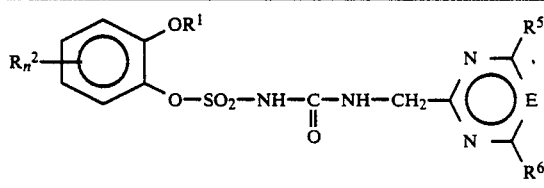

| Ex. No. | R¹ | R² | R⁵ | R⁶ | E | n | m.p. |
|---|---|---|---|---|---|---|---|
| 516 | CH₂CH₃ | H | OCH₃ | OCH₃ | CH | 0 | |
| 517 | CH₂CH₃ | H | OCH₃ | CH₃ | CH | 0 | |
| 518 | CH₂CH₃ | H | OCH₃ | CH₃ | N | 0 | |
| 519 | CH₂CH₂CH₃ | H | OCH₃ | OCH₃ | CH | 0 | |
| 520 | CH₂CH₂CH₃ | H | OCH₃ | CH₃ | CH | 0 | |
| 521 | CH₂CH₂CH₃ | H | OCH₃ | CH₃ | N | 0 | |
| 522 | CH(CH₃)₂ | H | OCH₃ | OCH₃ | CH | 0 | |
| 523 | CH(CH₃)₂ | H | OCH₃ | CH₃ | CH | 0 | |
| 524 | CH(CH₃)₂ | H | OCH₃ | CH₃ | N | 1 | |
| 525 | CH₂CH₃ | 6-CH₃ | OCH₃ | CH₃ | N | 1 | |
| 526 | CH₂CH₂CH₃ | 6-OCH₃ | OCH₃ | OCH₃ | CH | 1 | |
| 527 | CH(CH₃)₂ | 6-Cl | OCH₃ | CH₃ | N | 1 | |
| 528 | CH₂CH₃ | 6-CF₃ | OCH₃ | CH₃ | CH | 1 | |
| 529 | CH₂CH₂CH₃ | 6-F | OCH₃ | OCH₃ | N | 1 | |
| 530 | CH(CH₃)₂ | 6-OCF₂H | OCH₃ | CH₃ | CH | 1 | |

TABLE 7

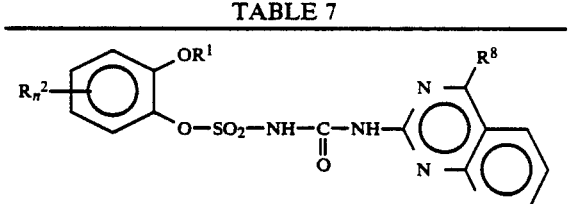

| Ex. No. | R¹ | R² | R⁸ | n | m.p. |
|---|---|---|---|---|---|
| 531 | CH₂CH₃ | H | OCH₃ | 0 | |
| 532 | CH₂CH₃ | H | CH₃ | 0 | |
| 533 | CH₂CH₂CH₃ | H | OCH₃ | 0 | |
| 534 | CH₂CH₂CH₃ | H | CH₃ | 0 | |
| 535 | CH(CH₃)₂ | H | OCH₃ | 0 | |
| 536 | CH(CH₃)₂ | H | CH₃ | 0 | |

TABLE 7-continued $$R_n^2 \underset{}{\overset{OR^1}{\longleftrightarrow}} O-SO_2-NH-\underset{O}{\overset{\|}{C}}-NH-\underset{N}{\overset{N}{\longleftrightarrow}} \overset{R^8}{\underset{N}{\longleftrightarrow}}$$

| Ex. No. | $R^1$ | $R^2$ | $R^8$ | n | m.p. |
|---|---|---|---|---|---|
| 537 | $CH_2CH_3$ | 6-$CH_3$ | $CH_3$ | 1 | |
| 538 | $CH_2CH_2CH_3$ | 6-$OCH_3$ | $CH_3$ | 1 | |
| 539 | $CH(CH_3)_2$ | 6-Cl | $OCH_3$ | 1 | |
| 540 | $CH_2CH_3$ | 6-$CF_3$ | $CH_3$ | 1 | |
| 541 | $CH_2CH_2CH_3$ | 6-F | $OCH_3$ | 1 | |
| 542 | $CH(CH_3)_2$ | 6-$OCF_2H$ | $CH_3$ | 1 | |

TABLE 8

$$R_n^2 \underset{}{\overset{OR^1}{\longleftrightarrow}} O-SO_2-NH-\underset{O}{\overset{\|}{C}}-NH-\underset{N}{\overset{N}{\longleftrightarrow}}\underset{R^{11}}{\overset{R^8}{\underset{N}{\longleftrightarrow}}}\underset{}{\overset{}{\longleftrightarrow}}R^7$$

| Ex. No. | $R^1$ | $R^2$ | $R^7$ | $R^8$ | $R^{11}$ | n | m.p. |
|---|---|---|---|---|---|---|---|
| 543 | $CH_2CH_3$ | H | H | $OCH_3$ | H | 0 | |
| 544 | $CH_2CH_3$ | H | H | $CH_3$ | $CH_3$ | 0 | |
| 545 | $CH_2CH_3$ | H | $CH_3$ | $CH_3$ | $CH_3$ | 0 | |
| 546 | $CH_2CH_2CH_3$ | H | H | $OCH_3$ | H | 0 | |
| 547 | $CH_2CH_2CH_3$ | H | H | $CH_3$ | $CH_3$ | 0 | |
| 548 | $CH_2CH_2CH_3$ | H | $CH_3$ | $CH_3$ | $CH_3$ | 0 | |
| 549 | $CH(CH_3)_2$ | H | H | $OCH_3$ | H | 0 | |
| 550 | $CH(CH_3)_2$ | H | H | $CH_3$ | $CH_3$ | 0 | |
| 551 | $CH(CH_3)_2$ | H | $CH_3$ | $CH_3$ | $CH_3$ | 0 | |
| 552 | $CH_2CH_3$ | 6-$CH_3$ | H | $CH_3$ | H | 1 | |
| 553 | $CH_2CH_2CH_3$ | 6-$OCH_3$ | H | $CH_3$ | $CH_3$ | 1 | |
| 554 | $CH(CH_3)_2$ | 6-Cl | $CH_3$ | $OCH_3$ | $CH_3$ | 1 | |
| 555 | $CH_2CH_3$ | 6-$CF_3$ | H | $CH_3$ | H | 1 | |
| 556 | $CH_2CH_3$ | 6-F | H | $OCH_3$ | $CH_3$ | 1 | |
| 557 | $CH(CH_3)_2$ | 6-Cl | $CH_3$ | $CH_3$ | $CH_3$ | 1 | |

BIOLOGICAL EXAMPLES

The damage on the weed plants and the tolerance by crop plants were scored using a key where numbers from 0 to 5 express the activity. In this key 0 denotes no action
1 denotes 0–20% action or damage
2 denotes 20–40% action or damage
3 denotes 40–60% action or damage
4 denotes 60–80% action or damage
5 denotes 80–100% action or damage

1. Pre-emergence action on weeds

Seeds or rhizome pieces of monocotyledon and dicotyledon weed plants were placed in plastic pots containing sandy loam soil and covered with soil. Various dosages of aqueous suspensions or emulsions of the compounds according to the invention formulated as wettable powders or emulsion concentrates were then applied to the surface of the cover soil, at an application rate of water of 600–800 l/ha (converted).

After the treatment, the pots were placed in the greenhouse and maintained at good growth conditions for the weeds. Visual scoring of the damage to plants or of the emergence damage was carried out after the emergence of the test plants after a trial period of 3 to 4 weeks, comparing them to untreated control plants. As shown by the score data in Table 9, the compounds according to the invention have good herbicidal pre-emergence activity against a broad range of weed grasses and broad leaf weeds.

2. Post-emergence action on weeds

Seeds or rhizome pieces of monocotyledon and dicotyledon weeds were placed in plastic pots in sandy loam ground, covered with soil and grown in the greenhouse under good growth conditions. Three weeks after sowing, the test plants were treated in the three-leaf stage.

Various dosages of the compounds according to the invention formulated as wettable powders or emulsion concentrates were sprayed onto the green parts of the plants, at an application rate of water of 600–800 l/ha (converted), and the action of the preparations was scored visually after the test plants had remained in the greenhouse for about 3 to 4 weeks under optimum growth conditions, comparing them to untreated control plants.

The agents according to the invention exhibit a good herbicidal activity against a broad range of economically important weed grasses and broad-leaf weeds, also in the post-emergence treatment (Table 10).

3. Tolerance by crop plants

In further greenhouse experiments, seeds of a relatively large number of crop plants and weeds were placed in sandy loam ground and covered with soil.

Some of the pots were treated immediately as described under 1., those remaining were placed in the greenhouse until the plants had developed two to three true leaves and were then sprayed with various dosages of the substances according to the invention as described under 2.

Four to five weeks after application, with the plants remaining in the greenhouse, visual scoring revealed that the compounds according to the invention did not cause any damage to dicotyledon crops, such as, for example, soya beans, cotton, oilseed rape, sugar beet and potatoes when applied both as a pre-emergence and post-emergence treatment, even at high dosages of active substance. Furthermore, Gramineae crops such as, for example, barley, wheat, rye, sorghum millet, maize or rice, were also unaffected by some of the substances. Thus, the compounds of the formula I exhibit high selectivity on application for controlling undesired plant growth in agricultural crops.

TABLE 9

Pre-emergence action of the compounds according to the invention

| Ex. No. | Dosage in Kg of a.i./ha | Herbicidal action | | | | | |
|---|---|---|---|---|---|---|---|
| | | SIA | CRS | STM | AS | ECG | LOM |
| 2 | 0,6 | 5 | 5 | 5 | 1 | 3 | 4 |
| 3 | 0,6 | 5 | 5 | 5 | 2 | 3 | 3 |
| 4 | 0,6 | 5 | 5 | 4 | 4 | 4 | 1 |
| 5 | 0,6 | 5 | 4 | 4 | 2 | 2 | 1 |
| 7 | 0,6 | 5 | 5 | 3 | 2 | 2 | 2 |
| 75 | 0,6 | 5 | 5 | 5 | 2 | 2 | 2 |
| 104 | 0,3 | 5 | 5 | 5 | 1 | 3 | 1 |
| 133 | 0,3 | 5 | 5 | 5 | 4 | 5 | 5 |
| 137 | 0,3 | 5 | 5 | 5 | 2 | 4 | 2 |
| 138 | 0,3 | 5 | 5 | 5 | 5 | 4 | 5 |
| 153 | 0,3 | 5 | 5 | 5 | 3 | 3 | 4 |
| 163 | 0,3 | 5 | 5 | 5 | 4 | 4 | 5 |

TABLE 9-continued

Pre-emergence action of the compounds according to the invention

| Ex. No. | Dosage in Kg of a.i./ha | Herbicidal action | | | | | |
|---|---|---|---|---|---|---|---|
| | | SIA | CRS | STM | AS | ECG | LOM |
| 321 | 0,3 | 5 | 5 | 5 | 1 | 2 | 1 |

TABLE 10

Post-emergence action of the compounds according to the invention

| Ex. No. | Dosage in Kg of a.i./ha | Herbicidal action | | | | | |
|---|---|---|---|---|---|---|---|
| | | SIA | CRS | STM | AS | ECG | LOM |
| 2 | 0,6 | 5 | 5 | 5 | 0 | 4 | 5 |
| 3 | 0,6 | 5 | 5 | 5 | 1 | 4 | 4 |
| 4 | 0,6 | 5 | 4 | 4 | 3 | 4 | 2 |
| 5 | 0,6 | 5 | 5 | 4 | 2 | 2 | 3 |
| 7 | 0,6 | 5 | 5 | 5 | 1 | 3 | 2 |
| 75 | 0,6 | 5 | 5 | 5 | 0 | 5 | 3 |
| 104 | 0,3 | 5 | 5 | 5 | 3 | 4 | 3 |
| 133 | 0,3 | 5 | 5 | 5 | 3 | 5 | 5 |
| 137 | 0,3 | 5 | 4 | 5 | 2 | 4 | 2 |
| 138 | 0,3 | 5 | 5 | 5 | 4 | 5 | 4 |
| 153 | 0,3 | 5 | 4 | 5 | 2 | 4 | 2 |
| 163 | 0,3 | 5 | 5 | 5 | 4 | 4 | 5 |
| 321 | 0,3 | 4 | 5 | 5 | 1 | 3 | 1 |

Abbreviations:
SIA = *Sinapis alba*
CRS = *Chrysanthemum segetum*
STM = *Stellaria media*
AS = *Avena sativa*
ECG = *Echinochloa crus-galli*
LOM = *Lolium multiflorum*
a.i. = active substance

We claim:
1. A compound of formula I, or a salt thereof,

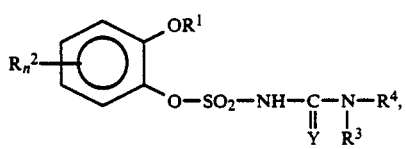
(I)

wherein
$R^1$ is ethyl, propyl or isopropyl,
$R^2$ is halogen, $NO_2$, $CF_3$, $CN$, $(C_1-C_4)$alkyl, $(C_1-C_4)$alkoxy, $(C_1-C_4)$alkylthio or $[(C_1-C_4)$alkoxy]carbonyl,
n is 0, 1, 2 or 3,
Y is O or S,
$R^3$ is hydrogen, $(C_1-C_8)$alkyl, $(C_2-C_8)$alkenyl, $(C_2-C_8)$alkynyl, or $(C_1-C_4)$alkoxy,
$R^4$ is heterocyclic radical of the formula

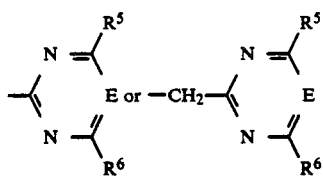

E is CH
$R^5$ and $R^6$ independently of one another are hydrogen, $(C_1-C_6)$alkyl, $(C_1-C_6)$alkoxy, $(C_1-C_6)$alkylthio, it being possible for the above-mentioned alkyl-containing radicals to be monosubstituted or polysubstituted by halogen or monosubstituted or disubstituted by $(C_1-C_4)$alkoxy, or $(C_1-C_4)$alkylthio, or furthermore are a radical of formula $NR^{12}R^{13}$, $-OCHR^7-CO_2R^{12}$, $(C_3-C_6)$cycloalkyl, $(C_3-C_5)$alkenyl, $(C_2-C_4)$alkynyl, $(C_3-C_5)$alkenyloxy or $(C_3-C_5)$alkynyloxy,
$R^7$ is hydrogen or $(C_1-C_4)$alkyl, and
$R^{12}$ and $R^{13}$ independently of one another are hydrogen, $(C_1-C_4)$alkyl, $(C_2-C_4)$alkenyl or $(C_3-C_4)$alkynyl.

2. A compound of the formula I or a salt thereof as claimed in claim 1, wherein
n is 0 or 1,
Y is O,
$R^2$ is oriented in the 6-position of the phenyl ring and is fluorine, chlorine, $(C_1-C_4)$alkyl, $(C_1-C_4)$alkoxy or $[(C_1-C_4)$alkoxy]-carbonyl,
$R^3$ is hydrogen, $(C_1-C_4)$alkyl, $(C_3-C_4)$alkenyl,
$R^4$ is a heterocyclic radical of the formula

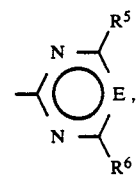

and $R^5$ and $R^6$ independently of one another are $(C_1-C_4)$alkyl, $(C_1-C_4)$alkoxy, $(C_1-C_4)$alkylthio, it being possible for the above-mentioned alkyl-containing radicals to be monosubstituted or polysubstituted in the alkyl moiety by halogen or monosubstituted or disubstituted by $(C_1-C_4)$alkoxy or $(C_1-C_4)$alkylthio.

3. A compound as claimed in claim 2, wherein $R^5$ and $R^6$ independently of one another are methyl or methoxy.

4. A compound as claimed in claim 2 wherein $R^1$ is $CH_2CH_3$, $R^2$ is 6-$COOCH_3$, $R^3$ is H, $R^5$ is $OCH_3$, $R^6$ is $CH_3$, E is CH and n is 1.

5. A compound as recited in claim 2, wherein $R^1$ is $CH_2CH_3$, $R^2$ is $CF_3$, $R^3$ is H, $R^5$ is $OCH_3$, $R^6$ is $CH_3$, E is CH and n is 1.

6. A compound as recited in claim 1, wherein $R^1$ is $CH_2CH_3$, $R^2$ is $CF_3$, $R^3$ is H, $R^4$ is

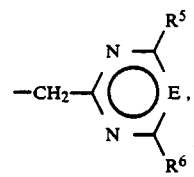

$R^5$ is $OCH_3$, $R^6$ is $CH_3$, E is CH and n is 1.

7. A herbicidal composition comprising a herbicidally effective amount of one or more compounds as claimed in claim 1, or salts thereof, and an inert carrier therefor.

8. A plant growth regulating composition comprising a plant growth regulating effective amount of one or more compounds as claimed in claim 1, or salts thereof, and an inert carrier therefor.

9. A method for controlling noxious plants which comprises applying a herbicidally effective amount of one or more compounds as claimed in claim 1, or salts thereof, to a noxious plant or soil used in agriculture or industry.

10. A method for regulating the growth of crop plants which comprises applying a growth regulating effective amount of one or more compounds as claimed in claim 1, or salts thereof, to a crop plant or an area of cultivation of said crop plant.

11. A compound as in claim 2, wherein Y is oxygen, and $R^3$ is hydrogen, and n is 0 or 1, and $R^5$ and $R^6$ independently of one another are $(C_1-C_4)$alkyl or $(C_1-C_4)$alkoxy.

12. A compound as in claim 11, wherein $R^1$ is ethyl, n is 0, $R^5$ is methoxy and $R^6$ is methoxy.

13. A compound as in claim 11, wherein $R^1$ is isopropyl, n is 0, $R^5$ is methoxy and $R^6$ is methoxy.

14. A compound as in claim 11, wherein $R^1$ is ethyl, n is 1, $R^2$ is 6-chloro, $R^5$ is methoxy and $R^6$ is methoxy.

15. A compound as in claim 11, wherein $R^1$ is ethyl, n is 1, $R^2$ is 6-chloro, $R^5$ is methoxy and $R^6$ is methoxy.

16. A compound as in claim 11, wherein $R^1$ is ethyl, n is 1, $R^2$ is 6-methoxy, $R^5$ is methoxy and $R^6$ is methoxy.

17. A compound as in claim 11, wherein $R^1$ is ethyl, n is 1, $R^2$ is 6-methyl, $R^5$ is methoxy and $R^6$ is methoxy.

18. A compound as in claim 11, wherein $R^1$ is ethyl, n is 1, $R^2$ is 6-methoxycarbonyl, $R^5$ is methoxy and $R^6$ is methoxy.

* * * * *